(12) United States Patent
Novak et al.

(10) Patent No.: US 12,278,004 B2
(45) Date of Patent: Apr. 15, 2025

(54) CLINICAL DATA HARVESTER

(71) Applicant: Optum, Inc., Minnetonka, MN (US)

(72) Inventors: Edward Thomas Novak, Signal Mountain, TN (US); Brandon Joshua Gilzean, Cary, NC (US); George Edward Bier, Richfield, MN (US); Eli Mitchell Wolter, Maple Grove, MN (US)

(73) Assignee: Optum, Inc., Minnetonka, MN (US)

( * ) Notice: Subject to any disclaimer, the term of this patent is extended or adjusted under 35 U.S.C. 154(b) by 250 days.

(21) Appl. No.: 17/653,836

(22) Filed: Mar. 7, 2022

(65) Prior Publication Data

US 2023/0123662 A1  Apr. 20, 2023

Related U.S. Application Data

(60) Provisional application No. 63/262,559, filed on Oct. 14, 2021.

(51) Int. Cl.
*G16H 10/60* (2018.01)
*G16H 40/20* (2018.01)
*G16H 50/20* (2018.01)

(52) U.S. Cl.
CPC ............ *G16H 10/60* (2018.01); *G16H 40/20* (2018.01); *G16H 50/20* (2018.01)

(58) Field of Classification Search
CPC ......... G16H 10/60; G16H 50/20; G16H 40/20
See application file for complete search history.

(56) References Cited

U.S. PATENT DOCUMENTS

| | | |
|---|---|---|
| 8,055,514 B2 | 11/2011 | Elsholz |
| 8,412,542 B2 | 4/2013 | Mok et al. |
| 8,766,803 B2 | 7/2014 | Bousamra et al. |
| 8,788,291 B2 | 7/2014 | Srinivasan et al. |
| 9,002,773 B2 | 4/2015 | Bagchi et al. |
| 10,529,445 B2 | 1/2020 | Cossler et al. |
| 10,978,188 B2 | 4/2021 | Givoly et al. |

(Continued)

FOREIGN PATENT DOCUMENTS

| | | | |
|---|---|---|---|
| KR | 20080012728 A | * | 2/2008 |
| WO | 2020/053863 A1 | | 3/2020 |

OTHER PUBLICATIONS

Wells et al., "Strategies for Handling Missing Data in Electronic Health Record Derived Data," eGEMS (Generating Evidence & Methods to improve patient outcomes), vol. 1, Issue 3, Article 7, Dec. 17, 2013, doi:10.13063/2327-9214.1035, 9 pp.

(Continued)

*Primary Examiner* — Raquel Alvarez
(74) *Attorney, Agent, or Firm* — Shumaker & Sieffert, P.A.

(57) ABSTRACT

A clinical harvester system may provision, based at least in part on information associated with a piece of clinical data associated with a user, a plurality of harvesters that query a plurality of data sources to locate the piece of clinical data. The clinical harvester system may transmit data between two or more of the plurality of harvesters as the plurality of harvesters query the plurality of data sources to communicate information used for locating the piece of clinical data within the plurality of data sources. The clinical harvester system may retrieve, using the plurality of harvesters, the piece of clinical data from one of the plurality of data sources.

20 Claims, 9 Drawing Sheets

(56) References Cited

U.S. PATENT DOCUMENTS

| | | | |
|---|---|---|---|
| 11,004,547 | B2 | 5/2021 | Valdes et al. |
| 2009/0299767 | A1 | 12/2009 | Michon et al. |
| 2012/0150558 | A1 | 6/2012 | Hasan et al. |
| 2012/0215560 | A1 | 8/2012 | Ofek et al. |
| 2013/0080192 | A1 | 3/2013 | Bucur et al. |
| 2013/0205227 | A1 | 8/2013 | Stevens et al. |
| 2013/0231946 | A1 | 9/2013 | Shibuya et al. |
| 2015/0213219 | A1 | 7/2015 | Antenen et al. |
| 2018/0046663 | A1 | 2/2018 | Guzman et al. |
| 2019/0391970 | A1 | 12/2019 | Rudser |
| 2020/0034933 | A1 | 1/2020 | Rolih et al. |
| 2020/0160946 | A1 | 5/2020 | Poblenz et al. |
| 2020/0227161 | A1 | 7/2020 | Hanson et al. |
| 2022/0101961 | A1 | 3/2022 | Ballard et al. |
| 2023/0085426 | A1* | 3/2023 | Athman ............... G16H 10/60 600/300 |
| 2023/0207076 | A1* | 6/2023 | Morris ............... G06F 40/205 705/3 |

OTHER PUBLICATIONS

International Search Report and Written Opinion of International Application No. PCT/US2022/077704 dated Dec. 15, 2022, 19 pp.
Regan et al., "Estimating influenza vaccine effectiveness using data routinely available in electronic primary care records", Vaccine, vol. 37, No. 5, Jan. 29, 2019, pp. 755-762.
International Preliminary Report on Patentability from International Application No. PCT/US2022/077704 dated Apr. 25, 2024, 9 pp.

* cited by examiner

CLINICAL DATA HARVESTER

This application claims the benefit of U.S. Provisional Patent Application No. 63/262,559, filed Oct. 14, 2021, the entire content of which is incorporated herein by reference.

BACKGROUND

A requester may obtain clinical data for a patient, such as immunization records or lab work results, by building a roster of patients into a file and transmitting the file to a submitter, such as a laboratory. The requester then waits for the submitter to retrieve and gather all the data for each of the patients on the roster and to transmit a file of results back to the requester. This process could take a full day up to weeks and months, depending on the number of patients on the roster.

SUMMARY

In general, this disclosure describes techniques for utilizing triggers to initiate harvesting of missing pieces of clinical data from internal and/or external data sources to retrieve the missing pieces of clinical data. Specifically, aspects of this disclosure describe a clinical harvester system that may provision a plurality of harvesters to query data sources to find and retrieve the missing pieces of clinical data. As the harvesters execute, the harvesters may communicate with each other to exchange information that may be useful for finding the missing pieces of clinical data and may provide feedback regarding the progress of the harvesters in finding and retrieving the missing pieces of clinical data.

In some aspects, the techniques described herein relate to a method including: provisioning, by one or more processors of a clinical harvester system and based at least in part on information associated with a piece of clinical data associated with a user, a plurality of harvesters that query a plurality of data sources to locate the piece of clinical data; transmitting, by the one or more processors, data between two or more of the plurality of harvesters as the plurality of harvesters query the plurality of data sources to communicate information used for locating the piece of clinical data within the plurality of data sources; and retrieving, by the one or more processors and using the plurality of harvesters, the piece of clinical data from one of the plurality of data sources.

In some aspects, the techniques described herein relate to a clinical harvester system including: a memory; and one or more processors configured to: provision, based at least in part on information associated with a piece of clinical data associated with a user, a plurality of harvesters that query a plurality of data sources to locate the piece of clinical data; transmit data between two or more of the plurality of harvesters as the plurality of harvesters query the plurality of data sources to communicate information used for locating the piece of clinical data within the plurality of data sources; and retrieve, using the plurality of harvesters, the piece of clinical data from one of the plurality of data sources.

In some aspects, the techniques described herein relate to a non-transitory computer-readable storage medium storing instructions that, when executed, cause one or more processors of a clinical harvester system to: provision, based at least in part on information associated with a piece of clinical data associated with a user, a plurality of harvesters that query a plurality of data sources to locate the piece of clinical data; transmit data between two or more of the plurality of harvesters as the plurality of harvesters query the plurality of data sources to communicate information used for locating the piece of clinical data within the plurality of data sources; and retrieve, using the plurality of harvesters, the piece of clinical data from one of the plurality of data sources.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description.

DETAILED DESCRIPTION

Figure 1A:
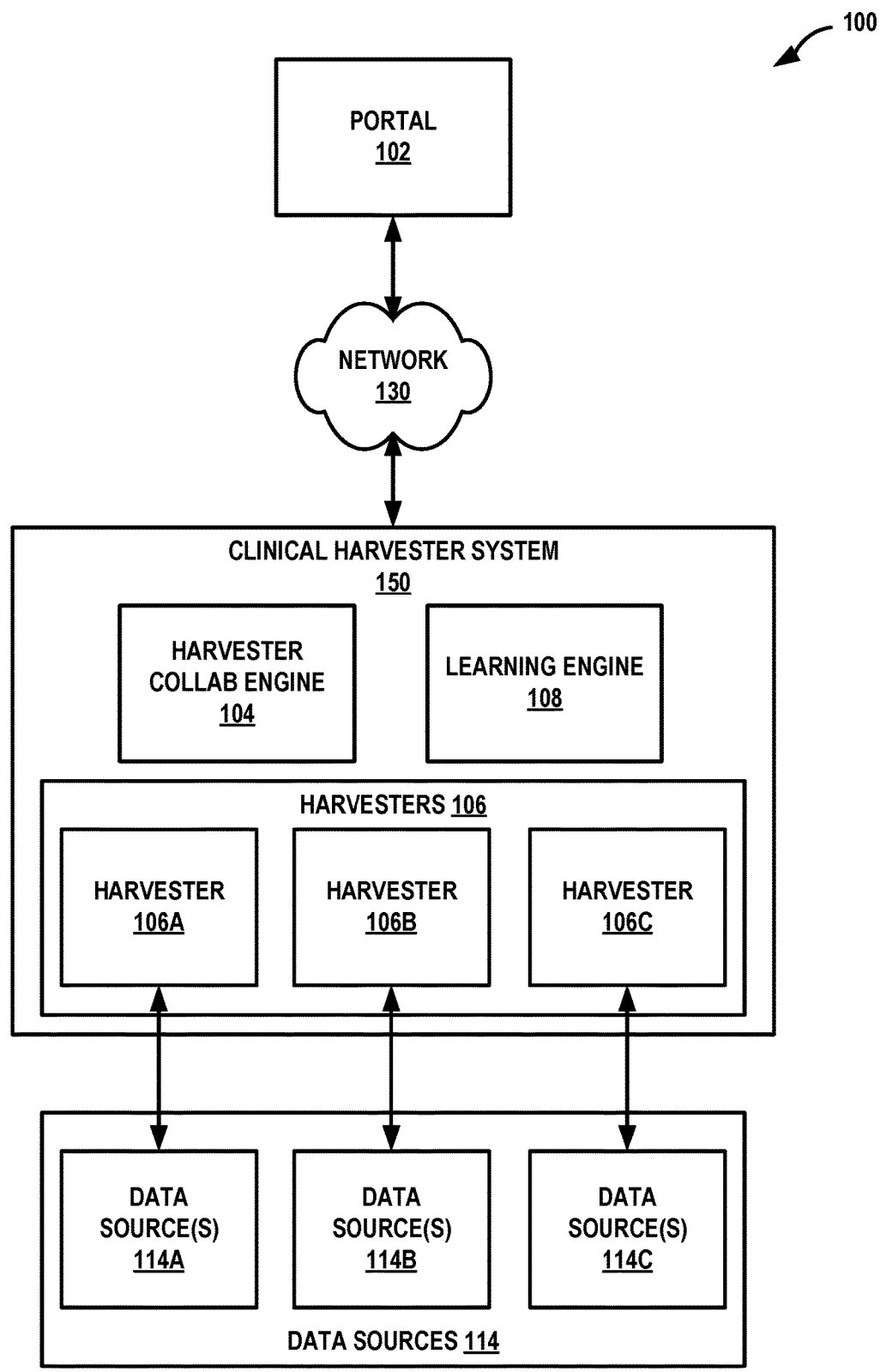
FIGS. 1A and 1B illustrates an environment that includes a clinical harvester system, in accordance with aspects of the present disclosure.

In general, aspects of this disclosure describe techniques for a clinical harvester system to search for and retrieve pieces of clinical data from data sources in ways that are more flexible and less resource intensive. A health provider, such as a healthcare provider, a health insurance provider, a clinic, a hospital, and the like, may receive requests for pieces of clinical data, such as immunization records, lab reports, drug prescription records, and the like. However, in certain situations, the health provider may be unable to locate and retrieve a requested piece of clinical data. For example, the health provider may not be able to determine the location of the piece of clinical data within data sources internal to the health provider, or the piece of clinical data may be located at a data sources external to the health provider. As such, the health provider may, upon determining that the health provider is unable to locate a requested piece of clinical data, use a clinical harvester system to search for and retrieve the requested piece of clinical data.

The clinical harvester system may not receive an indication of the specific data source that contains the piece of clinical data. Rather, the clinical harvester system may be configured to search through a variety of data sources, including data sources internal to the health provider as well as data sources external to the health provider to find and retrieve pieces of clinical data. The clinical harvester system may have to use a variety of different techniques to query such a wide variety of different data sources, such as issuing queries in different query languages, interfacing with different application programming interfaces (APIs), and the like. Further, the clinical harvester system may determine, based on the data retrieved from the data sources, that other data sources not currently being queried by the clinical harvester system may contain the piece of clinical data or may contain data that is relevant for finding the piece of clinical data. As such, the clinical harvester system may have to adaptively query new data sources as the clinical harvester system queries data sources to find pieces of clinical data.

In accordance with aspects of the present disclosure, the clinical harvester system may use harvesters that can be quickly spun up to query data sources to find and retrieve pieces of clinical data. The harvesters may be serverless applications that the clinical harvester system may provision as needed in a cloud-based system to query data sources for pieces of clinical data. By provisioning harvesters in the form of serverless applications, the clinical harvester system may avoid having to perform provisioning, scaling, and management of servers to provision the harvesters. Clinical harvester system may therefore be able to quickly provision harvesters as needed to adaptively query new data sources to find pieces of clinical data.

As the harvesters execute, the harvesters may communicate with each other to exchange information that may be useful for finding the missing pieces of clinical data. Harvesters may use such information received from other harvesters to more quickly find and retrieve clinical data, such as by determining specific data sources to query for the clinical data based on the received information, and by determining to refrain from querying certain data sources. In this way, the harvesters may dynamically determine, as the harvesters execute which data sources may or may not potentially store the clinical data as the harvesters, and the harvester may be able to reduce the number of data sources that the harvesters may have to query before finding the clinical data in one of the data sources. As such, the techniques described in this disclosure may increase the performance of the clinical harvester system by enabling the clinical harvester to be able to more quickly find and retrieve clinical data from a data source. Further, by enabling harvesters to reduce the number of data sources that the harvesters may have to query before finding the clinical data in one of the data sources, the techniques described in this disclosure may also reduce the amount of network traffic (e.g., queries and responses to queries) sent and received by the clinical harvester system, thereby improving the network utilization of the clinical harvester system.

Figure 1B:
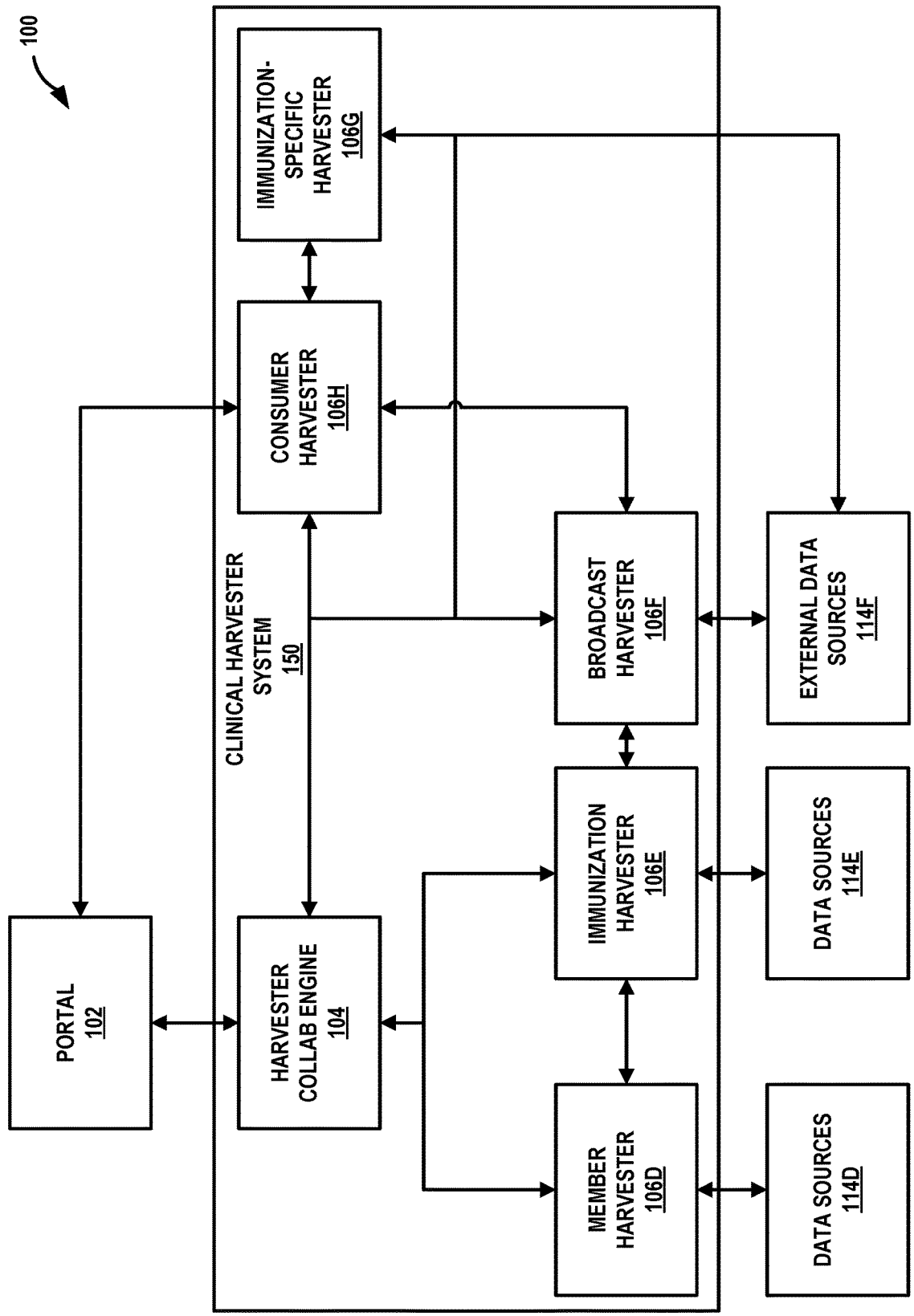

FIGS. 1A and 1B illustrates an environment 100 that includes a clinical harvester system 150, in accordance with aspects of the present disclosure. As shown in FIG. 1A, environment 100 includes clinical portal 102 and clinical harvester system 150 connected via network 130. Portal 102 and clinical harvester system 150 may be associated with a health provider such as a healthcare provider, a health insurance provider, a clinic, a hospital, and the like. Portal 102 is configured to execute at one or more processors of a computing device, such as a server, a mainframe, in the cloud, and the like to provide an interface (e.g., a graphical user interface), such as in the form of one or more web pages, dashboards, and the like with which users, such as members of the health provider associated with portal 102, may interact to request and receive clinical data associated with a user, such as immunization records, lab test results, electronic medical records, or any other clinical or medical data associated with a user.

In some examples, the interfaces provided by portal 102 may be in the form of programmatic interfaces, such as one or more Application Programming Interfaces (APIs). Users, such as members of the health provider associated with portal 102, administrators, people working for the health provider, and the like, may use applications that communicate via the APIs with portal 102 to send requests for clinical data to portal 102 and to receive the requested clinical data from portal 102.

Portal 102 associated with a health provider may, in response to receiving the request for clinical data from a user, attempt to retrieve the requested clinical data and output the requested clinical data for viewing by the user. Portal 102 may attempt retrieve such data from systems, data stores, and other sources associated with the health provider. However, portal 102 may not always be able to retrieve all of the pieces of the requested clinical data. For example, portal 102 may not be able to ascertain or otherwise determine the locations of pieces of the requested clinical data, or may otherwise be unable to access the pieces of the requested clinical data. Such pieces of the requested clinical data that portal 102 is unable to find and retrieve may be referred to herein as missing piece of clinical data.

Portal 102 may communicate with clinical harvester system 150 to use clinical harvester system 150 to find and retrieve the missing piece of clinical data. In some examples, clinical harvester system 150 includes one or more computing devices, such as server devices, mainframes, and the like. In some examples, clinical harvester system 150 is a cloud-based system. A cloud-based system may refer to a collection of computing devices (e.g., servers, mainframes, etc.) in a cloud infrastructure (e.g., using a server farm or cluster of high performance computers running software suitable for handling high volumes of requests from multiple users) that host applications that execute at the processors of the computing devices in the cloud-based system to provide one or more services to clinical portal 102 via network 130. In some examples, portal 102 may, in response to determining that portal 102 is unable to find and retrieve one or more pieces of the requested clinical data, portal 102 may send a request to clinical harvester to find the missing piece of clinical data.

In some examples, clinical harvester system 150 may listen to (i.e., access, in real-time) communications to and from portal 102 for events that may trigger clinical harvester system 150 to find and retrieve missing piece of clinical data. For example, clinical harvester system 150 may listen to requests for clinical data sent to portal 102 from applications and/or users to listen for requests for pieces of clinical data that clinical harvester system 150 determines portal 102 is unable to retrieve. Clinical harvester system 150 may, in response to determining that a request for clinical data sent to portal 102 includes a request for one or more pieces of clinical data that clinical harvester system 150 determines portal 102 is unable to retrieve, find and retrieve the requested one or more pieces of clinical data, and may return the requested one or more pieces of clinical data to portal 102.

Clinical harvester system 150 may be able to determine whether portal 102 is able to retrieve pieces of clinical data via any suitable technique. In some examples, clinical harvester system 150 may store a list of clinical data for which portal 102 is unable to retrieve. In some examples, clinical harvester system 150 may determine pieces of clinical data that portal 102 has previously been unable to retrieve. As clinical harvester system 150 listens to communications to and from portal 102, clinical harvester system 150 may listen for requests for pieces of clinical data that corresponds to the pieces clinical data that portal 102 has previously been unable to retrieve. Clinical harvester system 150 may, in response to detecting requests sent to portal 102 for pieces of clinical data that corresponds to the pieces clinical data that portal 102 has previously been unable to retrieve, find and retrieve the requested pieces of clinical data.

In some examples, portal 102 may return requested clinical data in the form of data streams, such as in the form of Kafka streams, and clinical harvester system 150 may listen to the data streams being returned by portal 102 to identify incomplete segments in the data streams that may indicate missing piece of clinical data. For example, if portal 102 returns a data stream that includes fields that contain pieces of requested clinical data, then empty fields in the data stream may indicate missing piece of clinical data. Clinical harvester system 150 may therefore listen to the data stream to identify empty fields to determine the missing piece of clinical data that clinical harvester system 150 may find and retrieve. For example, if clinical harvester system 150 determines that the data stream returned by portal 102 contains an empty field for the flu immunization records of a user, clinical harvester system 150 may determine that the flu immunization records of the user is the missing piece of clinical data that clinical harvester system 150 may find, retrieve, and return to portal 102.

Portal 102 and clinical harvester system 150 may communicate via network 130. Network 130 represents any public or private communications network, for instance, cellular, Wi-Fi, and/or other types of networks, for transmitting data between computing systems, servers, and computing devices. Network 130 may include one or more network hubs, network switches, network routers, or any other network equipment, that are operatively inter-coupled thereby providing for the exchange of information between clinical harvester system 150 and clinical portal 102. Clinical harvester system 150 and clinical portal 102 may transmit and receive data across network 130 using any suitable communication techniques. Clinical harvester system 150 and clinical portal 102 may each be operatively coupled to network 130 using respective network links. The links coupling clinical harvester system 150 and clinical portal 102 to network 130 may be Ethernet or other types of network connections and such connections may be wireless and/or wired connections.

Clinical harvester system 150 includes harvester collaboration engine 104, harvesters 106, and learning engine 108, each of which may be software applications that execute at one or more processors of clinical harvester system 150. Harvester collaboration engine 104 is configured to coordinate the execution and use of harvesters 106 to find and retrieve missing piece of clinical data. For example, harvester collaboration engine 104 may, in response to determining that the clinical data returned by portal 102 includes a missing piece of clinical data, such as when portal 102 is unable to find and retrieve one or more pieces of clinical data (i.e., missing piece of clinical data), harvester collaboration engine 104 may spin up (e.g., provision) two or more of harvesters 106 to search for and find the missing pieces clinical data.

Harvesters 106 may be applications that execute at one or more processors of clinical harvester system 150 to ingest, process, and output records at scale to search for and find pieces of clinical data. Harvesters 106 may be deployed in a serverless environment in the cloud via technologies such as Kubernetes, Kafka, Docker, and the like. For example, harvesters 106 may be deployed as serverless applications on Kubernetes, such as via use of Knative. In some examples, harvesters 106 may also be architected according to Lambda architecture to handle large quantities of data. Harvesters 106 may listen for events and, in response, query data sources for clinical data based on the events and immediately publish data (e.g., clinical data) retrieved from such data sources to a data stream. Harvesters 106 may provide some potential advantages. For example, harvesters 106 may be serverless and platform-agnostic, may have zero downtime for deployment and/or configuration changes, and may enable proactive clinical data acquisition.

Furthermore, harvesters 106 may be configurable via use of configuration files, which may be written using, for example, YAML. The configuration files may configure the specific data sources to be queried by each of harvesters 106, the types of data that is to be exchanged between harvesters 106. In addition, the configuration files may configure, for a harvester, how the harvester prioritizes data received from other harvesters in selecting data sources, how the harvester queries one or more data sources, heuristics for determining whether a piece of information is relevant for finding the piece of clinical data, and the like.

Harvesters 106 In some examples, harvesters 106 may be part of a harvester farm, which may, include one or more virtual containers, such as Docker containers, that performs ingestion, processing, and distribution. For example, each harvester of harvesters 106 may be deployed as a virtual container image (e.g., a Docker image) in the harvester farm, and clinical harvester system 150 may provision a harvester by running the virtual container image associated with the harvester to create a virtual container (e.g., a Docker container) to execute the provisioned harvester.

Each harvester of harvesters 106 may be configured to query one or more of data sources 114 to find and retrieve a specific category of data that may be related to the missing piece of clinical data. In the example of FIG. 1A, harvesters 106 includes harvesters 106A-106C, data sources 114 includes one or more data sources 114A-114C. Harvester 106A may therefore be configured to query one or more data sources 114A, harvester 106B may be configured to query one or more data sources 114B, and harvester 106C may be configured to query one or more data sources 114C. In some examples, harvester collaboration engine 104 may, as part of provisioning each data harvester of data harvesters 106, specify the one or more of data sources 114 that each provisioned data harvester is to query to find and retrieve data. That is, harvester collaboration engine 104 may specify that harvester 106A is to query one or more data sources 114A, harvester 106B is to query one or more data sources 114B, and harvester 106C is to query one or more data sources 114C.

Data sources 114 may include structured and unstructured data stores, databases, services, applications, web sites, servers, storage systems, the cloud, and the like. Example types of data that can be stored in data sources 114 include electronic health records, electronic medical records, records of patient encounters, lab work results, membership information for health providers, drug prescription claims, immunization records, medical claims, rosters, and the like. Data sources 114 may include one or more data sources internal to the health provider associated with portal 102 and clinical harvester system 150. That is, one or more data sources of data sources 114 may be data sources internal to an organization that includes portal 102 and clinical harvester system. Data sources 114 may also include one or more data sources external to the health provider associated with portal 102 and clinical harvester system 150. That is, one or more data sources of data sources 114 may be data sources that is not within an organization that includes portal 102 and clinical harvester system.

For example, harvesters 106 may include a member harvester configured to query one or more of data sources 114 to find and retrieve information related to a user's membership in the health provider associated with clinical harvester system 150, such as demographics information (e.g., name, date of birth, height, weight, etc.) of the user, eligibility information associated with the user such as the healthcare plan that the user is a member of, and the like, an immunization harvester configured to query one or more of data sources 114 to find and retrieve immunization records associated with the user, a claims harvester configured to query one or more data sources to find and retrieve medical claims associated with the user, such as prescription claims, lab work claims, medical claims, and the like.

Harvester collaboration engine 104 may provision harvesters 106 based at least in part on the missing piece of clinical data that is to be retrieved by harvesters 106. For example, harvester collaboration engine 104 may determine whether the missing piece of clinical data includes clinical data associated with a member of the health provider associated with clinical harvester system 150, such as based on whether information associated with the missing piece of clinical data received by portal 102 includes an indication of a membership identifier associated with the health provider. Harvester collaboration engine 104 may, in response to determining that the information associated with the missing piece of clinical data received by portal 102 includes an indication of a membership identifier associated with the health provider, provision a membership harvester to find and retrieve information related to a user's membership in the health provider.

In another example, harvester collaboration engine 104 may determine the category of the missing piece of clinical data and may, in response, provision a harvester associated with the category of the missing piece of clinical data. For example, harvester collaboration engine 104 may, in response to determining that the missing piece of clinical data includes immunization records for a user, provision an immunization harvester to find and retrieve the immunization records associated with the user. In another example, harvester collaboration engine 104 may, in response to determining that the missing piece of clinical data includes lab work results for a user, provision a clinical harvester to find and retrieve the lab work results associated with the user.

The harvesters 106 provisioned by harvester collaboration engine 104 may execute in parallel to find and retrieve the missing piece of clinical data from one or more of data sources 114. As harvesters 106 execute to find and retrieve data, harvesters 106 may transmit data between each other to communicate information used for locating the clinical data. For example, the membership harvester may query, using the indication of a membership identifier associated with the health provider that is included in the information associated with the missing piece of clinical data, one or more data sources for information regarding the user associated with the missing piece of clinical data, such as demographics information of the user, the first and last name of the user, the birth date of the user, and the like.

The membership harvester may therefore transmit such information regarding the user associated with the missing piece of clinical data to the immunization harvester for use in retrieving immunization records associated with the user. A harvester may be able to use the information transmitted from another harvester to query one or more of data sources 114 to find and retrieve clinical data. For example, if different data sources of data sources 114 contain immunization records for members of different health insurance plans, the immunization harvester may use information regarding the health insurance plan of the user as determined by the membership harvester to select a data source associated with the health insurance plan of the user to query for the user's immunization records out of a plurality of different data sources that contain immunization records of users, thereby reducing the number of data sources that the immunization harvester may have to query to find the user's immunization records. In another example, the immunization harvester may be able to use the first and last name of the user retrieved by the membership harvester and transmitted to the immunization harvester to query one or more data sources to find and retrieve the immunization records associated with the user. In this way, two or more of harvesters 106 may communicate as the two or more harvesters execute to exchange data that may be useful for finding the missing piece of clinical data.

Each of harvesters 106 may be able to cache relevant data retrieved from data sources 114 and/or received from other harvesters. For example, the immunization harvester may determine and cache information regarding which of data sources 114 may contain relevant data for finding and retrieving clinical data (e.g., immunization records). When the immunization harvester is re-used by clinical harvester system 150 in the future to find other immunization records, the immunization harvester may service such requests using the cached information regarding which of data sources 114 may contain relevant data for finding and retrieving clinical data to select one or more data sources of data sources 114 to find the missing clinical data.

In some examples, harvesters 106 may be able to determine the relevancy of data cached by harvesters 106 and may, in response to determining that a piece of data cached by harvesters 106 is no longer relevant, discard (e.g., delete) the piece of data. For example, if the immunization harvester determines that the harvester is unable to use a piece of data cached by the immunization harvester for finding and retrieving clinical data, the immunization harvester may determine that the cached piece of data is no longer relevant and may delete the cached data. For example, the immunization harvester may cache a mapping of health insurance providers to specific data sources 114, so that the immunization harvester may, in response to determining the health insurance provider of a user, determine, based on the mapping, a specific data source associated with the health insurance provider to query to find the missing piece of clinical data. However, if the immunization harvester determines that the cached mapping is out of date, the immunization harvester may delete the mapping from the cache.

As harvesters 106 execute, harvesters 106 may track the paths taken by harvesters 106 when attempting to find the piece of clinical data. That is, each of harvesters 106 may track the specific data sources already queried by harvesters 106 and whether the harvesters 106 were able to find relevant data for finding the piece of clinical data from the queried data sources. By tracking the paths already taken, harvester 106 may refrain from re-querying data sources that have already been previously queried. Further, harvesters 106 may communicate with each other regarding the paths tracked by harvesters 106 to prevent other harvesters from re-querying data sources that have already been previously queried.

As harvesters 106 provisioned by harvester collaboration engine 104 execute to find and retrieve the missing piece of clinical data, harvesters 106 may communicate with harvester collaboration engine 104 to update harvester collaboration engine 104 on the statuses of the plurality of harvesters in finding and retrieving the missing piece of clinical data and to provide feedback regarding the search for the missing piece of clinical data. In some examples, the plurality of harvesters may update harvester collaboration engine 104 regarding the data sources from which the plurality of harvesters was able to find and retrieve information useful for finding and retrieving the missing piece of clinical data, and the data sources from which the plurality of harvesters were not able to find and retrieve information useful for finding and retrieving the missing piece of clinical data. For example, if an immunization harvester queries a plurality of data sources for the immunization records for the user, the immunization harvester may report back to harvester collaboration engine 104 regarding the result of querying each of the plurality of data sources for the immunization records for the user.

Learning engine 108 may use the feedback received by harvester collaboration engine 104 from the plurality of harvesters to improve the functionality of clinical harvester system 150 to find and retrieve missing piece of clinical data. Learning engine 108, in some examples, may include one or more neural networks trained to determine, based on information associated with missing piece of clinical data, one or more of data sources 114 that are likely to contain the missing piece of clinical data. In general, one or more neural networks implemented by learning engine 108 may include multiple interconnected nodes, and each node may apply one or more functions to a set of input values that correspond to one or more features, and provide one or more corresponding output values that are upper thresholds for each of a plurality of memory metrics. For instance, one or more neural networks may include one or more learnable parameters or "weights" that are applied to the features, and such learnable parameters may be adjusted during the training to improve the accuracy with which one or more neural networks determines one or more of data sources 114 that are likely to contain the missing piece of clinical data.

Learning engine 108 may use the feedback received by harvester collaboration engine from the plurality of harvesters as training data to improve the accuracy of learning engine 108 to predict one or more data sources 114 that are likely to contain the missing piece of clinical data. For example, the feedback received by harvester collaboration engine from the plurality of harvesters may include an association of the missing piece of clinical data, the user associated with the missing piece of clinical data, a data source, and an indication of whether the data source contains the missing piece of clinical data. Learning engine 108 may use the associations of the missing piece of clinical data, information regarding the user associated with the missing piece of clinical data, a data source, and an indication of whether the data source contains the missing piece of clinical data as training data to train learning engine 108 to determine, based on information associated with missing piece of clinical data, one or more of data sources 114 that are likely to contain the missing piece of clinical data.

Harvest collaboration engine 104 may use learning engine 108 to determine the specific harvesters of harvesters 106 to provision and/or use learning engine 108 to determine the specific one or more of data sources 114 to be queried by the specific harvesters to find and retrieve missing piece of clinical data. For example, harvest collaboration engine 104 may, in response to determining to find and retrieve a missing piece of clinical data, input information associated with the clinical data into learning engine 108. Such information may include the category of the clinical data (e.g., immunization records, lab work results, prescription information, etc.), information regarding the user associated with the clinical data (e.g., member information), and the like. Learning engine 108 may, in response to receiving such inputted information, output indications of one or more harvesters and/or one or more data sources that are likely to contain the missing piece of clinical data. Harvest collaboration engine 104 may therefore provision one or more of harvesters 106 and may, based on the indications of one or more data sources that are likely to contain the missing piece of clinical data outputted by learning engine 108, specify that the one or more of harvesters 106 query the one or more of data sources 114 indicated by the output of learning engine 108.

FIG. 1B illustrates a specific example in which clinical harvester system 150 may be used to search for and retrieve missing immunization data for a user. As shown in FIG. 1B, portal 102 may receive, from a user (e.g., a patient of a health provider associated with portal 102), a request for the user's immunization records and may, in response, output the user's immunization records for viewing by the user. The user may view their immunization records outputted by portal 102 and may determine that the user's immunization records as outputted by portal 102 do not include records of a recent vaccination, and may therefore provide user input at portal 102 that indicates the records of a recent vaccination of the user is missing from the user's immunization records. Portal 102 may receive the user input and determine, based on the user input, that records of a recent vaccination is missing from the user's immunization records. Portal 102 may, in response to determining that the recent vaccination of the user is missing from the user's immunization records, communicate with clinical harvester system 150 to find the missing vaccination records of the user.

Portal 102 may send, to harvester collaboration engine 104 of clinical harvester system 150, a request to find a missing piece of clinical data which, in the example, of FIG. 1B, may be a request to find the missing vaccination records of the user, as well as any other information portal 102 is able to determine that may be useful for finding the missing vaccination records of the user. Such information sent by portal 102 to harvester collaboration engine 104 may include, for example, information regarding the user who is missing their vaccination records, such as the name of the user, a user identifier (e.g., the username used by the user to log into portal 102), membership information regarding the user's membership in the health provider associated with portal 102, the other vaccination records of the user that portal 102 is able to find and retrieve, and the like.

Clinical harvester system 150 may, in response to receiving the information from portal 102, determine, based at least in part on the information received from portal 102, the harvesters to be used to find the missing piece of clinical data. For example, harvester collaboration engine 104 may determine, based on the information received from portal 102, that certain information regarding the user is missing and may therefore determine that member harvester 106D may be used to find additional data regarding the user. For example, harvester collaboration engine 104 may receive, from portal 102, information that indicates the user logged into portal 102 using a profile that is associated with a health provider. Harvester collaboration engine 104 may determine, based on the user using a profile associated with a health provider, that the user is possibly a member of the health provider. Harvester collaboration engine 104 may therefore determine to provision member harvester 106D to retrieve information regarding the user's membership in the indicated health provider. Harvester collaboration engine 104 may also determine, based on the missing piece of clinical data being missing immunization records of a patient, that immunization harvester 106E may be used to find the missing immunization records. Harvester collaboration engine 104 may therefore provision (e.g., start execution of) member harvester 106D and immunization harvester 106E.

Member harvester 106D may gather information regarding the user that is requesting their immunization records, such as the first name, last name, date of birth, weight, height, etc. Member harvester 106D may also gather eligibility information that indicates whether the user is a member of the health provider (e.g., enrolled in a health insurance program provided by the health provider), information regarding the particular health care plan of which the user is a member, the membership identifier of the user for the particular health care plan that the user is a member of, and the like. Member harvester 106D may also gather any other member-specific information.

To gather such member information regarding the user, member harvester 106D may communicate with one or more data sources 114D that are internal to the health provider associated with portal 102 and clinical harvester system 150. Data sources 114D may include structured and unstructured data stores, databases, services, web sites, and the like, and member harvester 106D may communicate with such data sources by sending database queries, calling APIs of the data sources, sending messages to the data sources, and the like.

Immunization harvester 106E may search for immunization data and may retrieve immunization details that are specific to the user's recent vaccination. To gather such immunization data associated with the user, immunization harvester 106E may communicate with one or more data sources 114E that are internal to the health provider associated with portal 102 and clinical harvester system 150. Data sources 114E may include structured and unstructured data stores, databases, services, web sites, and the like, and immunization harvester 106E may communicate with data sources 114E by sending database queries, calling APIs of the data sources, sending messages to the data sources, and the like.

Member harvester 106D and immunization harvester 106E may execute at the same time to find the missing piece of clinical data. That is, member harvester 106D and immunization harvester 106E may execute in parallel to communicate with respective one or more data sources 114D and 114E to find the missing piece of clinical data. As member harvester 106D and immunization harvester 106E execute, member harvester 106D and immunization harvester 106E may exchange data with each other and with any other harvesters that are executing to aid member harvester 106D and immunization harvester 106E to find the missing piece of clinical data. For example, if member harvester 106D and immunization harvester 106E execute at different computing devices in a cloud infrastructure, member harvester 106D and immunization harvester 106E may exchange data via a network.

The data exchanged between member harvester 106D and immunization harvester 106E may be tagged with an identifier to ensure the data being requested and retrieved by member harvester 106D and immunization harvester 106E are the same data referenced between member harvester 106D and immunization harvester 106E. In some examples, the identifier that tags the data exchanged between member harvester 106D and immunization harvester 106E may be associated with a particular piece of missing piece of clinical data, such as missing immunization records, so that communications between member harvester 106D and immunization harvester 106E regarding finding different pieces of missing piece of clinical data may be tags with different identifiers.

Member harvester 106D and immunization harvester 106E may communicate and exchange messages with each other to provide information to each other that may aid member harvester 106D and immunization harvester 106E with finding the missing immunization records for the user. For example, member harvester 106D may, in response to determining the first name and the last name of the user, communicate the first name and the last name of the user to immunization harvester 106E, and immunization harvester 106E may use the first name and the last name of the user received from member harvester 106D to query one or more data sources 114E in an attempt to find and retrieve the immunization records of the user.

As described above, member harvester 106D and immunization harvester 106E may each communicate with respective one or more data sources 114D and 114E that are internal to the health provider associated with portal 102 and clinical harvester system 150 in an attempt to find and retrieve immunization records of a user. Member harvester 106D and immunization harvester 106E may execute until clinical harvester system 150 determines whether the immunization records of the user exist in a data source internal to the health provider.

Member harvester 106D and immunization harvester 106E may continuously report back to harvester collaboration engine 104 regarding the progress of member harvester 106D and immunization harvester 106E in finding the immunization records of the user. In some examples, member harvester 106D and immunization harvester 106E may report back to harvester collaboration engine that member harvester 106D and immunization harvester 106E have been unable to find the immunization records within respective data sources 114D and 114E that are internal to the health provider associated with portal 102 and clinical harvester system 150. Harvester collaboration engine 104 may therefore determine that the immunization data does not exist in a data sources internal to the health provider, and harvester collaboration engine 104 may attempt to find the missing immunization records in a data source that is external to the health provider.

Harvester collaboration engine 104 may attempt to find the missing immunization records in a data source that is external to the health provider by provisioning broadcast harvester 106F that is configured to query one or more data sources 114F that are external to the health provider to find the missing immunization records. Such one or more data sources 114F may include a government immunization registry, an immunization database associated with a different health provider, and the like.

Broadcast harvester 106F may be configured to receive, from harvester collaboration engine 104, data retrieved by member harvester 106D and immunization harvester 106E, and to broadcast details of the missing immunization records to other harvesters, systems, and entities that may allow the other harvesters, systems, and entities to find the missing immunization records. As broadcaster harvester 106F executes, broadcast harvester 106F may communicate with other entities to indicate to the other entities that broadcast harvester 106F is searching for missing pieces of clinical data and to indicate to the other entities the time that it may take for the missing data to be found. That is, broadcast harvester 106F may track data lineage of the piece of clinical data, which may be a record of the intermediate steps and transformations of the data that took place as the piece of clinical data traveled through one or more systems, servers, and/or processes to be retrieved by clinical harvester system 150, to determine, based on the data lineage of the piece of clinical data, a data delivery time for delivering the piece of clinical data. Techniques used for tracking data lineage of pieces of clinical data are discussed with respect to FIG. 6.

In some examples, broadcast harvester 106F may communicate with immunization-specific harvester 106G provisioned by harvester collaboration engine 104 that is able to find and retrieve immunization records from one or more data sources, such as one or more data sources 114F, that are external to the health provider. Immunization-specific harvester 106G may query one or more data sources 114F for the missing immunization records and may, in response to finding the missing immunization records in one or more data sources 114F, retrieve the missing immunization records and send the retrieved missing immunization records to consumer harvester 106G. Consumer harvester 106G may therefore communicate with portal 102 to indicate that the missing immunization records have been found, and may transmit the missing immunization records to portal 102 for output.

As can be seen, according to the techniques of this disclosure, when a user requests health information (e.g., clinical data), harvesters are triggered to search for and find incomplete/missing data of the requested health information. The harvesters may communicate with each other to determine the pieces of data that are incomplete and/or missing from the requested health information and to determine where the incomplete/missing data can be located. The harvesters may determine whether the incomplete/missing data can be found within an entity internal to an organization or external to the organization and may retrieve the missing data by listening to events from an external entity in real-time. One or more of the harvesters may determine the time that it may take for the incomplete/missing data to be found by calculating the stops between the source of the data to a destination.

While aspects of the present disclosure describes clinical harvester system 150 have been described as being in a health care or clinical setting, this disclosure is not necessarily limited to the described health care or clinical settings to retrieve clinical data. Instead, clinical harvester system 150 can be used in a variety of non-health care and non-clinical environments and contexts to retrieve a wide variety of missing data. In some examples, the techniques of this disclosure are also applicable to retrieving any data on any services, servers, systems, etc.

Figure 2:
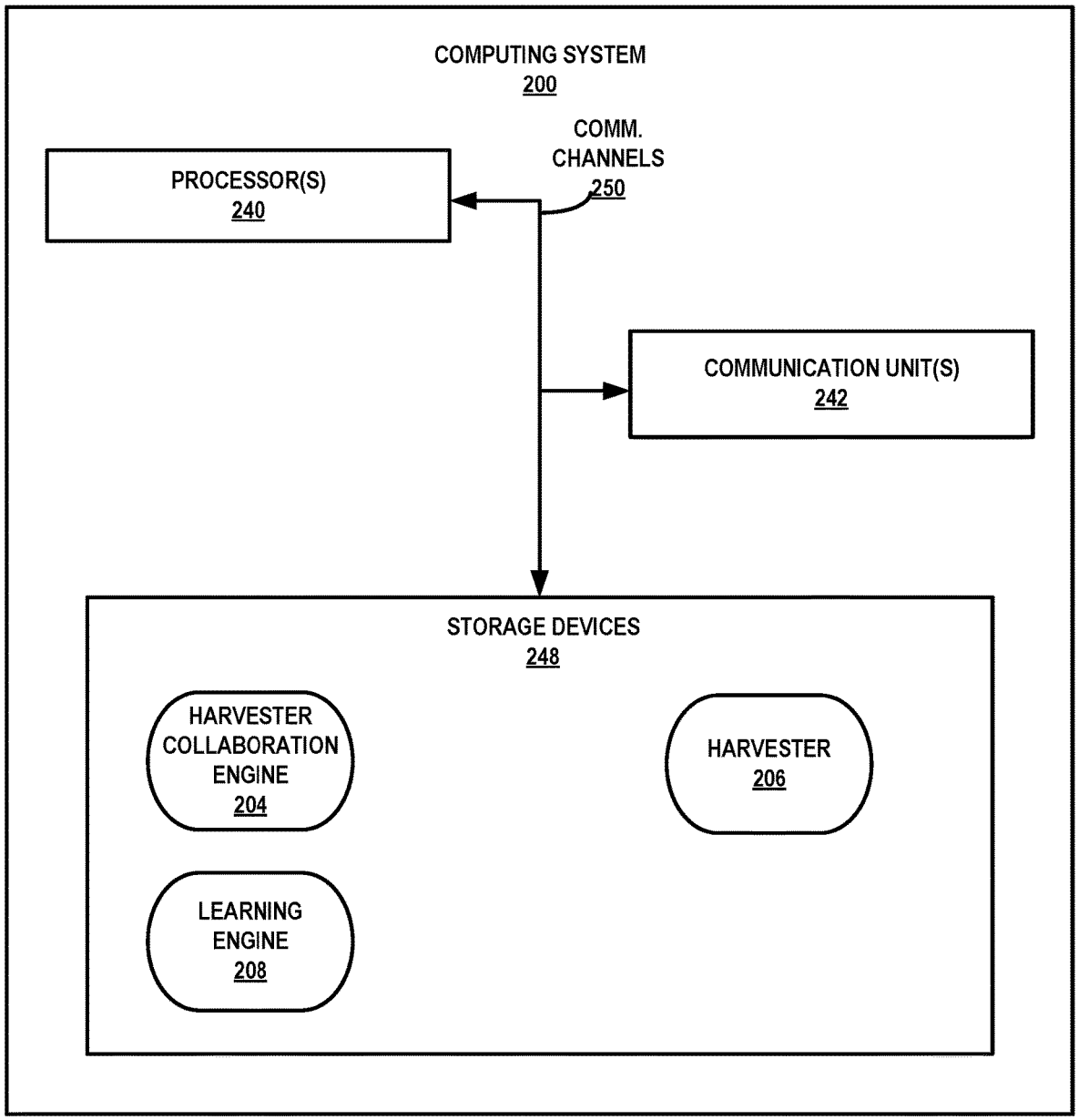
FIG. 2 is a block diagram illustrating details of a computing system, in accordance with one or more aspects of the present disclosure.

FIG. 2 is a block diagram illustrating details of a computing system, in accordance with one or more aspects of the present disclosure. As shown in FIG. 2, computing system 200 may be an example of computing devices that may execute any portions of the clinical harvester system 150 of FIGS. 1A and 1B. FIG. 2 illustrates only one particular example of a computing system, and many other examples of computing system may be used in other instances and may include a subset of the components included in example computing system 200 or may include additional components not shown in FIG. 2. In some example, clinical harvester system 150 of FIGS. 1A and 1B may execute at a cluster of servers, and each of the servers comprising the cluster of servers may include all, or some, of the components described herein in FIG. 2, to perform the techniques disclosed herein.

As shown in the example of FIG. 2, computing system 200 includes one or more processors 240, one or more communication units 242, and one or more storage devices 248. Storage devices 248 include harvester collaboration engine 204, harvester 206, and learning engine 208. In other words, storage device 248 may include computer-executable instructions associated with harvester collaboration engine 204, harvester 206, and learning engine 208. Communication channels 250 may interconnect each of the components 240, 242, and 248 for inter-component communications (physically, communicatively, and/or operatively). In some examples, communication channels 250 may include a system bus, a network connection, an inter-process communication data structure, or any other method for communicating data.

One or more communication units 242 of computing system 200 may communicate with external devices via one or more wired and/or wireless networks by transmitting and/or receiving network signals on the one or more networks. Examples of communication units 242 include a network interface card (e.g., such as an Ethernet card), an optical transceiver, a radio frequency transceiver, a global positioning satellite (GPS) receiver, or any other type of device that can send and/or receive information. Other examples of communication units 242 may include short wave radios, cellular data radios, wireless network radios, as well as universal serial bus (USB) controllers.

One or more storage devices 248 within computing system 200 may store information for processing during operation of computing system 200 (e.g., computing system 200 may store data accessed by harvester collaboration engine 204, harvester 206, and learning engine 208 during execution at computing system 200). In some examples, storage devices 248 is a temporary memory, meaning that a primary purpose of storage devices 248 is not long-term storage. Storage devices 248 of computing system 200 may be configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art.

Storage devices 248, in some examples, also include one or more computer-readable storage media. Storage devices 248 in some examples include one or more non-transitory computer-readable storage mediums. Storage devices 248 may be configured to store larger amounts of information than typically stored by volatile memory. Storage devices 248 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage devices 248 may store program instructions and/or information (e.g., data) associated with harvester collaboration engine 204, harvester 206, and learning engine 208. Storage devices 248 may include a memory configured to store data or other information associated with harvester collaboration engine 204, harvester 206, and learning engine 208.

One or more processors 240 may implement functionality and/or execute instructions associated with computing system 200. Examples of processors 240 include application processors, display controllers, auxiliary processors, one or more sensor hubs, and any other hardware configure to function as a processor, a processing unit, or a processing device. Harvester collaboration engine 204, harvester 206, and learning engine 208 may be operable by processors 240 to perform various actions, operations, or functions of computing system 200. For example, processors 240 of computing system 200 may retrieve and execute instructions stored by storage devices 248 that cause processors 240 to perform the operations of harvester collaboration engine 204, harvester 206, and learning engine 208.

Harvester collaboration engine 204 may include some or all of the functionalities of harvester collaboration engine 104 of FIGS. 1A and 1B. Harvester collaboration engine 204 may execute at one or more processors 240 to determine that a piece of clinical data is missing and to provision a plurality of harvesters, such as two or more of harvester 206, to find and retrieve the missing piece of clinical data. As the harvesters execute, harvester collaboration engine 204 may receive feedback from the harvesters regarding the search for the missing piece of clinical data, and harvester collaboration engine 204 may, in response, take one or more actions based on the feedback, such as provisioning additional harvesters to find and retrieve the missing clinical data.

Harvester 206 may include some or all of the functionalities of any of harvesters 106 in FIGS. 1A and 1B. Harvester 206 may be provisioned by harvester collaboration engine 204 to execute at one or more processors 240 to query one or more data sources to find the missing piece of clinical data. As harvester 206 executes, harvester 206 may exchange data with other harvesters to send and receive information to and from other harvesters to aid harvester 206 to find the missing piece of clinical data.

Learning engine 208 may include some or all of the functionalities of learning engine 108 of FIG. 1A. Learning engine 208 may execute at one or more processors 240 to use the feedback received by harvester collaboration engine 204 from harvesters to improve the functionality of the clinical harvester system. Learning engine 208, in some examples, may include one or more neural networks trained to determine, based on information associated with a missing piece of clinical data, one or more of data sources that are likely to contain the missing piece of clinical data. In general, one or more neural networks implemented by learning engine 208 may include multiple interconnected nodes, and each node may apply one or more functions to a set of input values that correspond to one or more features, and provide one or more corresponding output values that are upper thresholds for each of a plurality of memory metrics. For instance, one or more neural networks may include one or more learnable parameters or "weights" that are applied to the features, and such learnable parameters may be adjusted during the training to improve the accuracy with which one or more neural networks determines one or more of data sources that are likely to contain the missing piece of clinical data.

Learning engine 208 may execute at one or more processors 240 and may use the feedback received by harvester collaboration engine 204 from the plurality of harvesters as training data to improve the accuracy of learning engine 208 to predict one or more data sources that are likely to contain the missing piece of clinical data. For example, learning engine 208 may use associations of the missing piece of clinical data, information regarding the user associated with the missing piece of clinical data, a data source, and an indication of whether the data source contains the missing piece of clinical data as training data to train learning engine 208 to determine, based on information associated with missing piece of clinical data, one or more of data sources that are likely to contain the missing piece of clinical data.

Figure 3:
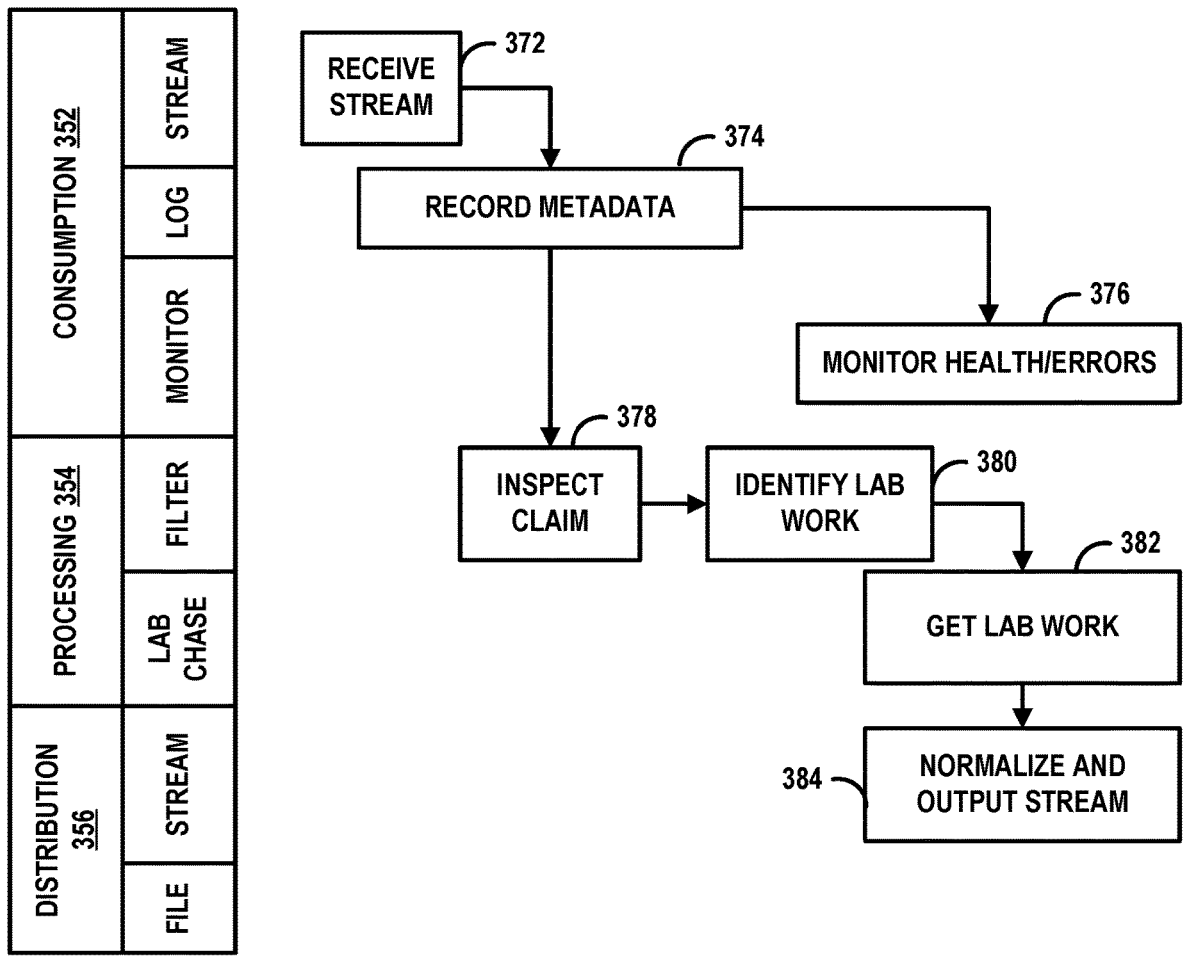
FIG. 3 illustrates the data flow of an example harvester farm, in accordance with aspects of the present disclosure.

FIG. 3 illustrates the data flow of an example harvester farm 300, in accordance with aspects of the present disclosure. As described above, a harvester farm such as harvester farm 300 may include a plurality of harvesters that perform ingestion, processing, and distribution of data streams in order to search for and retrieve clinical data. In some examples, a harvester farm such as harvester farm 300 can be implemented as a virtual container image, such as a Docker image.

In the example of FIG. 3, harvester farm 300 may be used to retrieve lab work results for patients in near real-time. Specifically, harvester farm 300 may use a lab chase service to find and retrieve lab work results for a specific health organization member and to chase down any other related lab work results. Harvester farm 300 may receive a stream of medical claims, process the information contained in the medical claims to determine that the medical claims include requests for lab work results, communicate with a lab chase service to find and retrieve the requested lab work results, and distribute the retrieved lab work results downstream.

As shown in FIG. 3, the data flow of harvester farm 300 may be in three phases: a consumption phase 352, a processing phase 354, and a distribution phase 356 of streams. During the consumption phase 352, harvester farm 300 may receive a stream (372). Such a stream may be a stream of a health care claims, such as health insurance claims, invoices for medical care, etc. In some examples, harvester farm 300 may receive streams in the form of Apache Kafka streams. Harvester farm 300 may, in response to receiving a stream, record metadata associated with the stream (374) and monitor the health of the harvesters in harvester farm 300 to ensure that the harvesters are running properly, such as monitoring the amount of memory used by the harvesters, the amount of processor usage by the harvesters, as well as determining whether any of the harvesters have stopped running or have otherwise failed (376).

After consumption phase 352, harvester farm 300 may transition to processing phase 354 to process the received stream. Specifically, if the received stream includes a health care claim, harvester farm 300 may inspect the claim in the stream (378) and may, based on inspecting the claim, identify that the claim requests a potential lab work result (380). In some examples, a harvester collaboration engine, such as harvester collaboration engine 104 of FIGS. 1A and 1B, may inspect the claim in the stream and may identify that the claim requests lab work results.

Harvester farm 300 may, in response to identifying that the claim requests lab work results, use a lab chase service to find and retrieve the requested lab work results (382). In some examples, a harvester collaboration engine may spin up a lab work harvester in harvester farm 300 to communicate with one or more lab chase services to find and retrieve the requested lab work results.

After consumption phase 352, harvester farm 300 may transition to distribution phase 356 to distribute downstream. Harvester farm 300 may distribute results by outputting a stream, such as an Apache Kafka stream, by writing the retrieved lab work results to a file, and the like. For example, harvester farm 300 may, in response to retrieving the requested lab work results, normalize and output the requested lab work results as a stream (384).

Figure 4A:
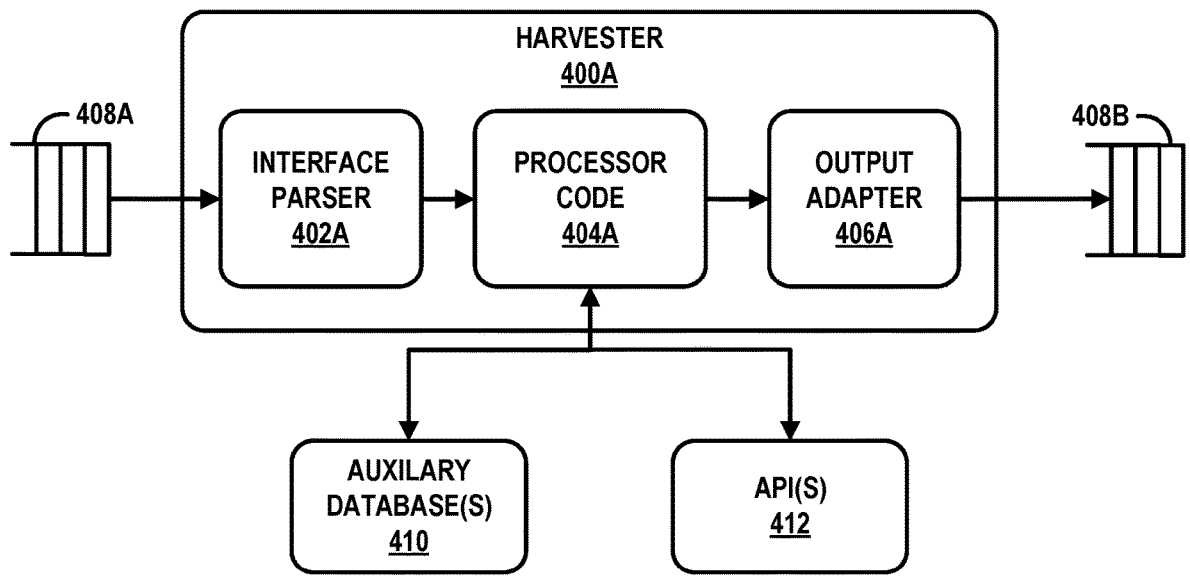
FIGS. 4A-4D illustrate example architectures of harvesters, in accordance with aspects of the present disclosure.

FIGS. 4A-4D illustrate example architectures of example harvesters, in accordance with aspects of the present disclosure. As shown in FIG. 4A, harvester 400A may be an example of any of the harvesters described throughout this disclosure, such as any one of harvesters 106 shown in FIGS. 1A and 1B. Harvester 400A may be architected to include interface parser 402A, processor code 404A, and output adapter 406A, where data may flow from interface parser 402A to processor code 404A to output adapter 406A. Harvester 400A may operate in accordance with a serverless processing pattern that enables ingestion, processing, and distribution of data streams at scale.

Interface parser 402A may be an input interface for harvester 400A to consume stream 408A. In the example where interface parser 402 consumes streams such as stream 408A, interface parser may be a stream interface. In the example where stream 408A is a Kafka stream, interface parser 402A may be a Kafka listener, and the listener endpoint, listener security, and logging by interface parser 402A may be defined by configuration. Stream 408A may include information that is associated with a missing piece of clinical data. In some examples, stream 408A may include data passed by other harvesters that execute in parallel with stream 408A which may be used by harvester 400A to find and retrieve a missing piece of clinical data.

Interface parser 402A may communicate with processor code 404A via messages, such as via JavaScript Object Notation (JSON), eXtensible Markup Language (XML), and the like, to pass information associated with stream 408A to processor code 404A. Such information associated with stream 408A may, in some examples, include data that may be used by processor code 404A to find and retrieve a missing piece of clinical data.

Processor code 404A may include code that executes at one or more processors to query data sources for missing clinical data based on stream 408A. Specifically, processor code 404A may execute to query one or more data sources to find and retrieve the missing clinical data. In the example of FIG. 4A, processor code 404A may communicate with one or more auxiliary databases 410 to find and retrieve the missing data. Processor code 404A may also utilize one or more application programming interfaces (APIs) 412 to communicate with one or more data sources to query the one or more data sources to find and retrieve the missing clinical data.

Processor code 404A may communicate with output adapter 406A to send the results of querying one or more data sources for the missing clinical data to output adapter 406A. The results of querying one or more data sources may include the missing clinical data retrieved by processor code 404A from one or more data sources and/or insights and other information determined by processor code 404A to be useful for finding the missing clinical data. Output adapter 406A may be a process that executes at one or more processors of a clinical harvester system to consume the information sent by processor code 404A and to distribute the information sent by processor code 404A in the form of stream 408B.

Figure 4B:
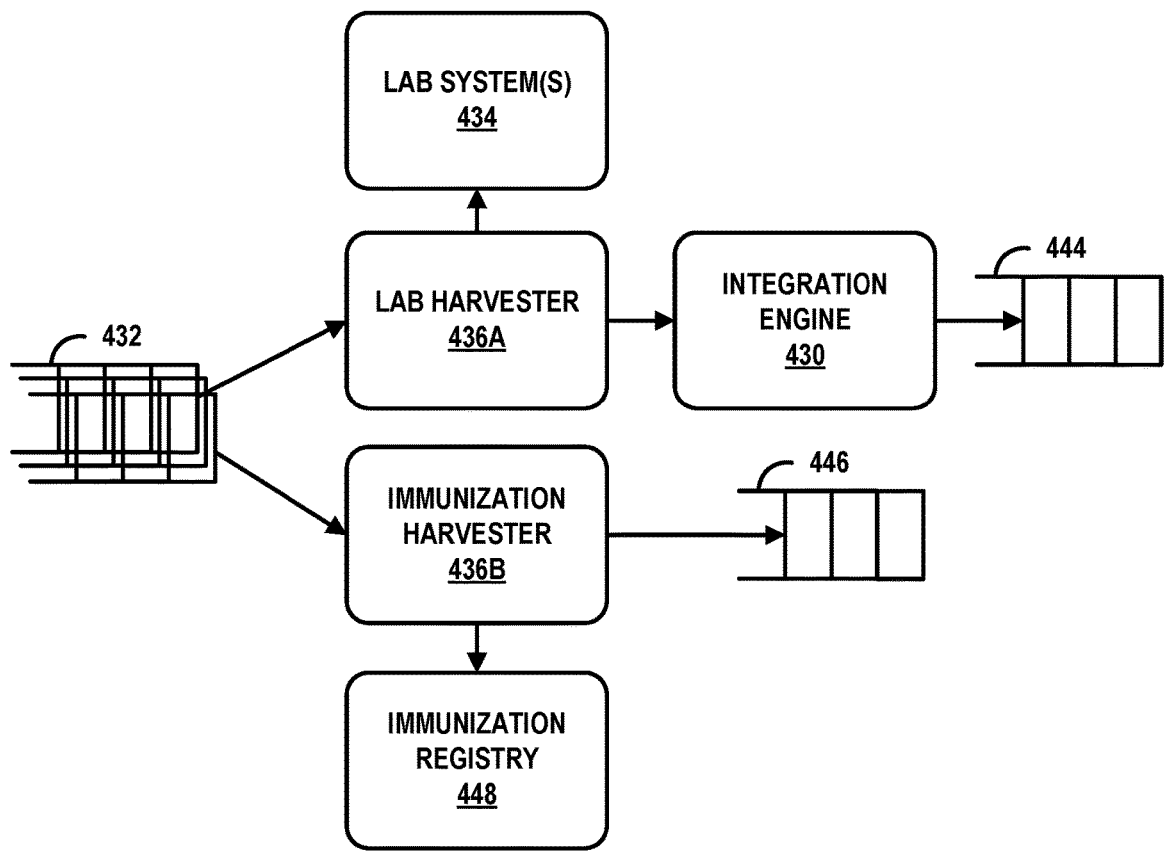

In some examples, multiple harvesters in a harvester farm may execute in parallel to consume and distribute data. As shown in FIG. 4B, lab harvester 436A may be a harvester that executes to find and retrieve lab work results while immunization harvester 436B may be a harvester that executes to find and retrieve immunization records. Lab harvester 436A and immunization harvester 436B may subscribe to stream 432 that may be a stream of health care provider claims. As lab harvester 436A and immunization harvester 436B consumes stream 432, lab harvester 436A and immunization harvester 436B may listen for events in the streams. Specifically, lab harvester 436A may listen for requests to find and retrieve lab work results in stream 432 and immunization harvester 436B may listen for requests to find and retrieve immunization records in stream 432.

As lab harvester 436A consumes stream 432, lab harvester 436A may service requests for lab work results included in stream 432 by communicating with one or more lab systems 434 to query one or more lab systems 434 for the requested lab work results. For example, lab harvester 436A may, for a request for lab work results in stream 432, also be able to determine from stream 432 or via other harvesters, information associated with the request for lab work results, such as an identifier of the patient that is requesting the lab work results. Such an identifier may be a name (e.g., first name and last name), health care provider member identification, and the like. Lab harvester 436A may use such information associated with the request for lab work results to query one or more lab systems 434 for the requested lab work results.

When lab harvester 436A receives the requested lab work results from one or more lab systems 434, lab harvester 436A may publish the requested lab work results to a data stream, such as stream 444. In some examples, lab harvester 436A may publish the requested lab work results via an integration engine 430 to stream 444. Integration engine 430 may be a software service that provides a framework for communicating patient information between health care organizations. One example of integration engine 430 is a Health Level 7 (HL7) engine.

Similarly, as immunization harvester 436B consumes stream 432, immunization harvester 436B may service requests for immunization records included in stream 432 by communicating with an immunization registry 448 to query immunization registry 448 for the requested immunization records. For example, immunization harvester 436B may, for a request for immunization records in stream 432, also be able to determine from stream 432 or via other harvesters, information associated with the request for immunization records, such as an identifier of the patient that is requesting the immunization records. Such an identifier may be a name (e.g., first name and last name), health care provider member identification, and the like. Immunization harvester 436B may use such information associated with the request for immunization records to query immunization registry 448 for the requested immunization records. When immunization harvester 436B receives the requested immunization records from immunization registry 448, immunization harvester 436B may publish the requested immunization records to a data stream, such as stream 446.

Figure 4C:
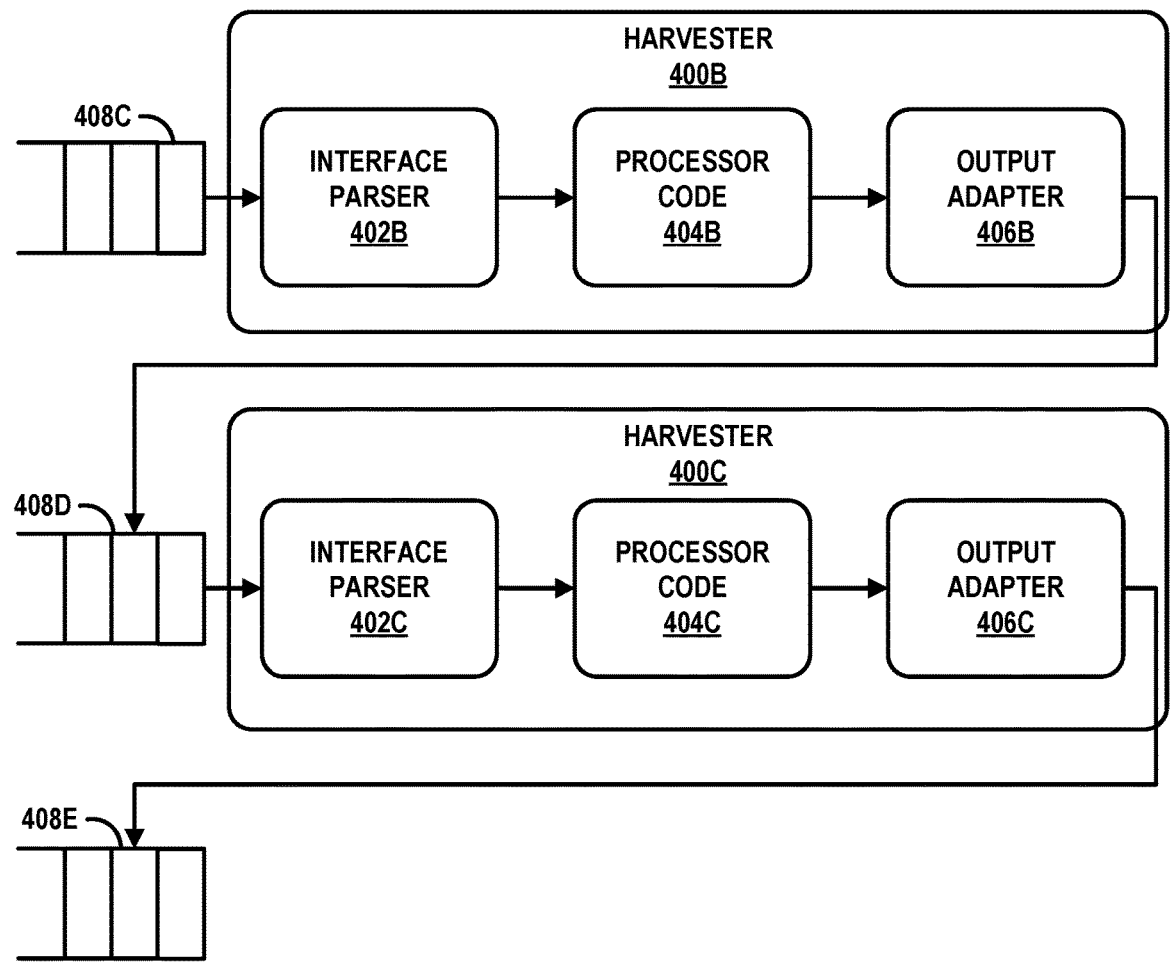

As described above, as harvesters in a harvester farm execute, the different harvesters may exchange messages with each other so that harvesters can publish data streams consumed by other harvesters and can consume data streams produced by other harvesters. In some examples, harvesters may be arranged in a chaining architecture. As shown in FIG. 4C, harvester 400B is changed with harvester 400C so that harvester 400C may consume stream 408D produced by harvester 400B.

In particular, interface parser 402B of harvester 400B may consume input data, such as in the form of stream 408C. Processor code 404B may process stream 408C, such as by querying one or more data sources to find and retrieve information requested in stream 408C, and output adapter 406B may output the information retrieved by processor code 404B as stream 408D.

Harvester 400C is chained to harvester 400B so that interface parser 402C of harvester 400C may consume stream 408D produced by harvester 400B. Processor code 404C may process stream 408D, such as by querying one or more data sources to find and retrieve information requested in stream 408D, and output adapter 406C may output the information retrieved by processor code 404C as stream 408E.

Figure 4D:
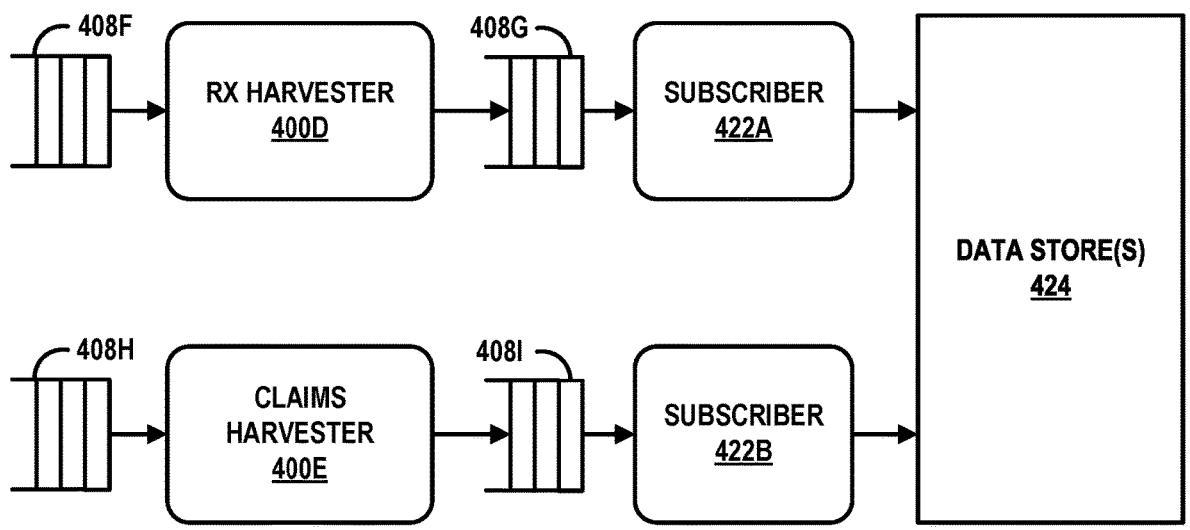

In some examples, harvesters may output data streams that are stored in data stores. As shown in FIG. 4D, prescriptions (Rx) harvester 400D may receive an Rx data stream 408F, which may include requests for prescription information for patient, and produce data stream 408G, which may be a data stream that contains the requested prescription information for patients. One or more data stores 424 may subscribe to data stream 408G produced by Rx harvester 400D, such as via subscriber 422A, and may store the data stream 408G produced by Rx harvester 400D.

Similarly, medical claims harvester 400E may receive a health care provider claims data stream 408H, which may be a data stream that contains requests for health care provider claims for patients, and may produce data stream 408I, which may be a data stream that contains the requested health care provider claims for patients. One or more data stores 424 may subscribe to data stream 408I produced by health care provider claims harvester 400E, such as via subscriber 422B, and may store the data stream 408I produced by health care provider claims harvester 400E.

One or more data stores 424 may include any suitable data store. In some examples, one or more data stores 424 may include one or more Spring Data Redis data stores, and subscribers 422A and 422B may be Spring Data Redis subscribers to enable the one or more data stores 424 to subscribe to data streams 408G and 408I.

Figure 5:
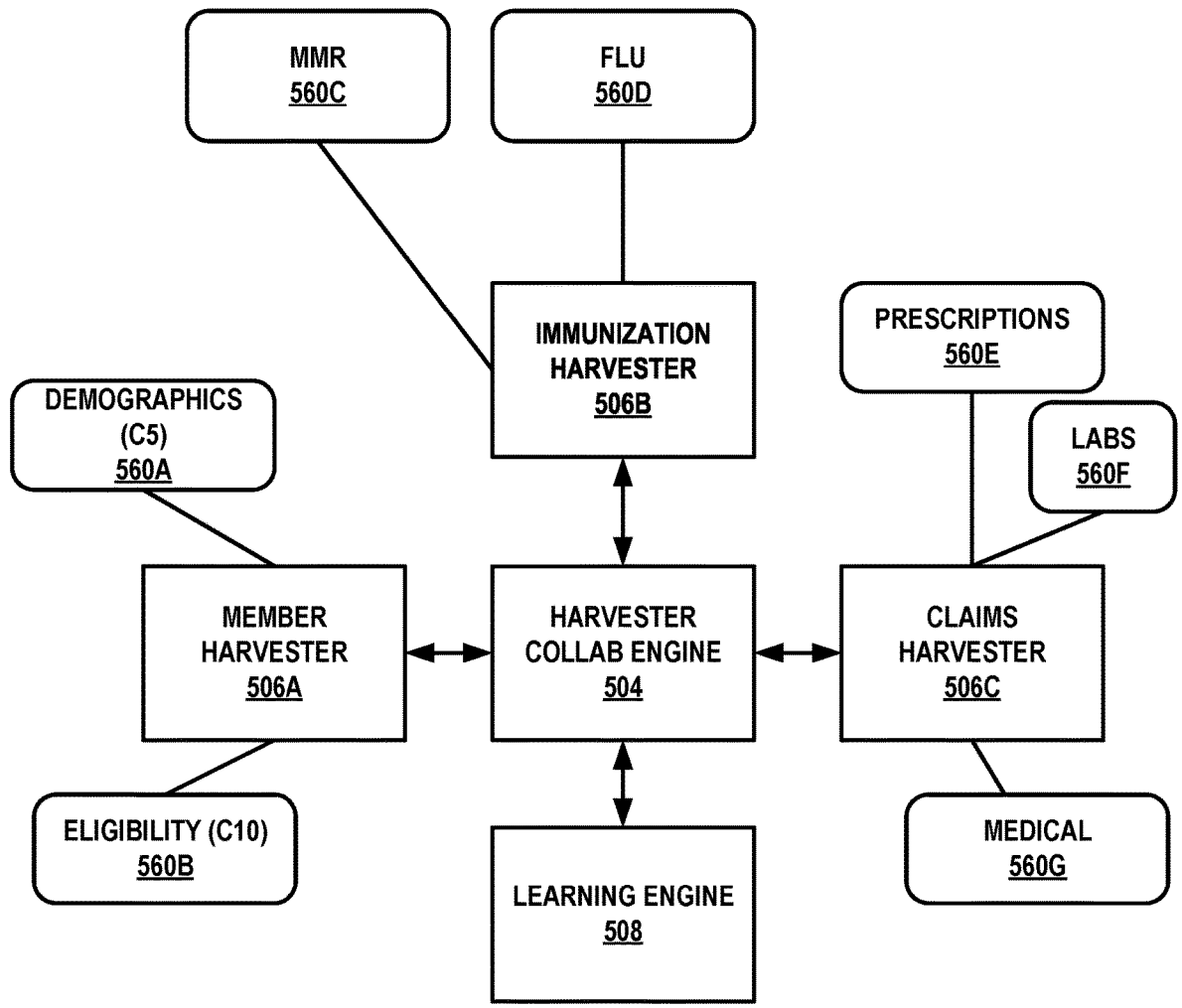
FIG. 5 illustrates confidence levels associated with data found by harvesters, in accordance with aspects of the present disclosure.

FIG. 5 illustrates confidence levels associated with data found by harvesters, in accordance with aspects of the present disclosure. As shown in FIG. 5, harvester collaboration engine 504, which is an example of harvester collaboration engine 104 of FIGS. 1A and 1B, may spin up and communicate with member harvester 506A, immunization harvester 506B, and claims harvester 506C, each of which may be an example of one or more of harvesters 106 of FIG. 1A, in response to receiving a request to find and return measles, mumps, and rubella (MMR) immunization records of a user.

Member harvester 506A may find and return information regarding the user for which harvesters 506A-506C are attempting to find immunization records, such as demographics information 560A for the user and eligibility information 560A for the user. Immunization harvester 506B may find and return immunization information for the user, such as MMR immunization information 560C for the user, flu immunization information 560D, and the like. Claims harvester 506C may find and return health insurance claims submitted by or otherwise associated with the user, such as prescriptions information 560E for the user, labs information 560F for the user, and medical information 560G for the user.

In some examples, the information found and retrieved by harvesters 506 may be associated with confidence scores. The confidence scores associated with a piece of information may correspond with the relevance of the information to finding a missing piece of clinical data. That is, a piece of information may be associated with a higher confidence score if the information is relatively more relevant to finding missing piece of clinical data, and a piece of information may be associated with a lower confidence score if the information is relatively less relevant to finding the missing piece of clinical data. A piece of information may be relevant to find a missing piece of clinical data if the piece of information can be used to determine the data source that contains the piece of clinical data. For example, if a piece of information specifies a particular health insurance associated with a user, the piece of information may indicate a particular immunization data source that is associated with the particular health insurance, such that, immunization harvester 506B may be able to use the piece of information to determine the data source that contains the MMR immunization information 560C for the user.

In the example of FIG. 5, each of information 560 may be associated with a confidence score from 1 to 10, where a confidence score of 10 may denote a very high level of confidence that the information is relevant to finding the information requested from harvester collaboration engine 504, and where a confidence score of 1 may denote a very low level of confidence that the information is relevant to finding the information requested from harvester collaboration engine 504. For example, eligibility information 560B (which may indicate the particular health care providers (e.g., doctors, clinics, hospitals, etc.) that are eligible to provide immunizations for the user) may be very useful for finding the MMR immunization records for the user and therefore may be associated with a confidence score of 10, while demographics information 560A may be less important for finding the MMR immunization records for the user and therefore may be associated with a confidence score of 5. Similarly, because the request received by harvester collaboration engine 504 was a request for MMR immunization records for the user, MMR immunization information 560C may be extremely relevant to the request for MMR immunization records for the user and may therefore be associated with a confidence score of 10, while flu immunization information 560D may not be relevant at all to the request for MMR immunization records for the user and may therefore be associated with a confidence score of 1.

The confidence scores associated with the information retrieved by harvesters 506 may be determined by harvesters 506, harvester collaboration engine 504, and/or learning engine 508. In some examples, harvesters 506, harvester collaboration engine 504, and/or learning engine 508 may determine the confidence score associated with a piece of information based at least in part on keyword matching. That is, harvesters 506, harvester collaboration engine 504, and/or learning engine 508 may determine whether a piece of information includes or is associated with a keyword that is included or associated with the missing piece of clinical data.

For example, member harvester 506A may find and retrieve demographics information 560A and eligibility information 560B and communicate, either directly or via harvester collaboration engine 504, the retrieved demographics information 560A and eligibility information 560B to immunization harvester 506B. Immunization harvester 506B may attempt to use demographics information 560A and eligibility information 560B to find MMR immunization information 560C.

Member harvester 506A may perform keyword matching to determine confidence scores associated with the retrieved demographics information 560A and eligibility information 560B. For example, the keywords associated with the request for MMR immunization records may include the words immunization, mumps, measles, and rubella. Member harvester 506A may therefore perform keyword matching to determine whether the retrieved demographics information 560A and eligibility information 560B include any of the keywords associated with the request for MMR immunization records. For example, member harvester 506A may determine that eligibility information 560B includes multiple keywords associated with MMR immunization records, and thus may assign a confidence score of 10 to eligibility information 560B. Meanwhile, member harvester 506A may determine that demographics information 560A includes only a single keyword of the multiple keywords associated with the request for MMR immunization records and may therefore assign a confidence score of 5 to demographics information 560A.

Immunization harvester 506B may prioritize use of demographics information 560A and eligibility information 560B to find the requested MMR immunization records. For example, because immunization information 560B is associated with a higher confidence score compared with demographics information 560A, immunization harvester 506B may attempt to use immunization information 560B to query data sources for MMR immunization records before attempting to use demographics information 560A to query data sources for MMR immunization records. Immunization harvester 506B may therefore use demographics information 560A and/or eligibility information 560B to find and retrieve MMR immunization information 560C and flu immunization information 560D.

Immunization harvester 506B may, based on its attempt to use demographics information 560A and eligibility information 560B to find MMR immunization information 560C, report back to harvester collaboration engine 504 regarding the relevance of demographics information 560A and eligibility information 560B were for finding MMR immunization information 560C, and harvester collaboration engine 504 may therefore assign confidence scores to demographics information 560A and eligibility information 560B.

In some examples, harvester collaboration engine 504 may also communicate the confidence scores assigned to demographics information 560A and eligibility information 560B to learning engine 508. As member harvester 506A, immunization harvester 506B, and claims harvester 506C execute to find and return information associated with the user, harvester collaboration engine 504 may communicate with learning engine 508, similar to learning engine 108 of FIG. 1A. Learning engine 508 may perform learning using such confidence score information to generate new insights that harvester collaboration engine 504 may utilize in the future to more quickly find and retrieve requested information.

For example, learning engine 508 may determine, based on the high confidence score associated with eligibility information 560B and the lower confidence score associated with demographics information 560A, that eligibility information 560B may be more useful for immunization harvester 506B to find and retrieve MMR immunization information. Learning engine 508 may update harvester collaboration engine 504 with such determinations made by learning engine 508.

Thus, when harvester collaboration engine 504 receives a subsequent request for the MMR immunization records for a user, harvester collaboration engine 504 may direct member harvester 506A to find eligibility information for the user, because such eligibility information may be more useful for immunization harvester 506B to find and retrieve MMR immunization information. In this way, harvester collaboration engine 504 and learning engine 508 may use confidence scores associated with pieces of information to more quickly be able to find and retrieve requested information. In this way, learning engine 508 may enable clinical harvester system 150 to continue to seek the shortest path to the missing piece of clinical data.

Figure 6:
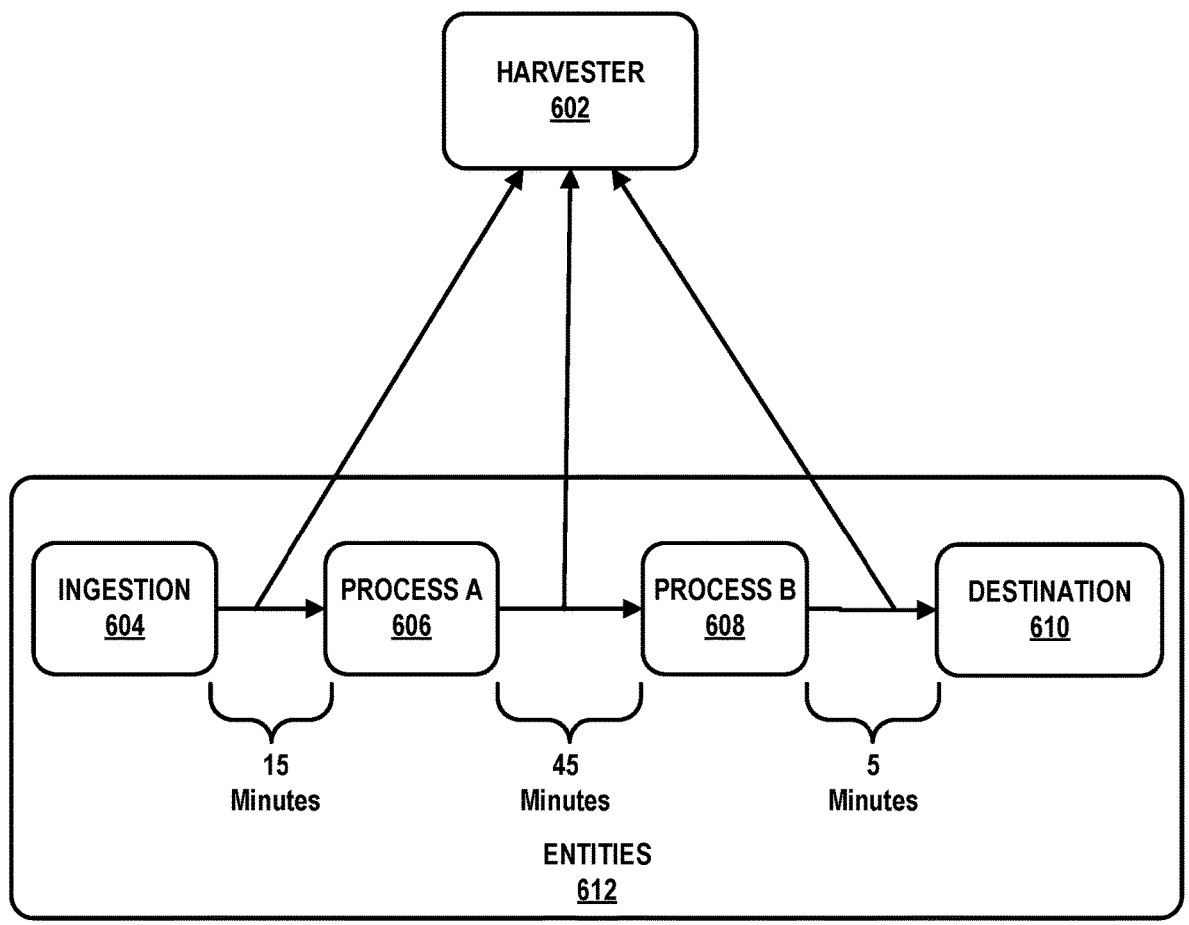
FIG. 6 illustrates determining data delivery times, in accordance with aspects of the present disclosure.

FIG. 6 illustrates determining data delivery times, in accordance with aspects of the present disclosure. As shown in FIG. 6, harvester 602 may communicate with one or more entities 612 to determine data delivery times of data (e.g., pieces of clinical data) from one or more entities 612. Harvester 602 may, upon determining the data delivery times of or more entities 612, be able to communicate the data delivery times to, for example, a clinical portal, such as portal 102 of FIGS. 1A-1B, in order to inform users of the data delivery times. Further, as the data delivery times change, harvester 602 may update portal 102 with updated data delivery times based on such changes to the data delivery times, so that portal 102 may be able to receive real-time information regarding the most up-to-date data delivery times for pieces of clinical data.

As described throughout this disclosure, a harvester, such as harvester 602, may communicate with internal entities and/or external entities, such as one or more entities 612, to find and retrieve requested information, such as clinical data. Harvester 602 may communicate one or more entities 612 by sending a query to the one or more entities 612 for the piece of information, such as lab work results, immunization records, a piece of clinical data, and the like. One or more entities 612 may, in response to receiving the query from harvester 602, process the query to return a piece of information.

In some examples, one or more entities 612 may perform a sequence of processes in order to process the query. For example, one or more entities 612 may first perform ingestion 604 to ingest the query, then perform process A 606, then perform process B 608, and then finally perform destination 610 to return the requested piece of information to harvester 602. In the example of FIG. 6, one or more entities may determine that it may take 15 minutes to complete ingestion, 45 minutes to complete process A 606, and 5 minutes to complete process B 608, for a total data delivery time of 65 minutes.

Harvester 602 may track the data lineage of a piece of information as one or more entities 612 processes a request to retrieve the piece of information and determine, based on the data lineage, the data delivery time for the piece of information. In some examples, one or more entities 612 may, in response to receiving a query from harvester 602, calculate the total data delivery time to return results associated with the query and may send an indication of the total data delivery time to harvester 602. That is, if one or more entities 612 determines that the total data delivery time is 65 minutes to return results associated with the query, one or more entities 612 may send an indication of 65 minutes to harvester 602. As one or more entities 612 performs the sequence of processes to process the query, one or more entities 612 may send indications of remaining data delivery times to harvester 602. For example, one or more entities 612 may, in response to completing ingestion 604, determine that the remaining data delivery time is 50 minutes, and may send an indication of 50 minutes to harvester 602. Similarly, one or more entities 612 may, in response to completing process A 606, determine that the remaining data delivery time is 5 minutes, and may send an indication of 5 minutes to harvester 602.

In some examples, harvester 602 may be able to calculate the data delivery time for a query based on information sent by one or more entities 612 to harvester 602. For example, one or more entities 612 may, in response to receiving a query from harvester 602, send, to harvester 602, indications of the sequence of processes for processing the query and the associated amount of time to complete each process in the sequence of processes. As harvester 602 performs the sequence of processes to process the query from one or more entities 612, one or more entities 612 may send, to harvester 602, updates regarding the completion of the sequence of processes to service the query. Thus, for example, one or more entities 612 may, upon completing ingestion 604, send, to harvester 602, an indication that ingestion 604 is complete. Harvester 602 may determine, based on the indication that ingestion 604 is complete, that one or more entities 612 may still have to perform process A 606 and process B 608, which may take another 50 minutes to complete. As such, harvester 602 may be able to determine, based on the indication that ingestion 604 is complete, that the remaining data delivery time is 50 minutes.

Figure 7:
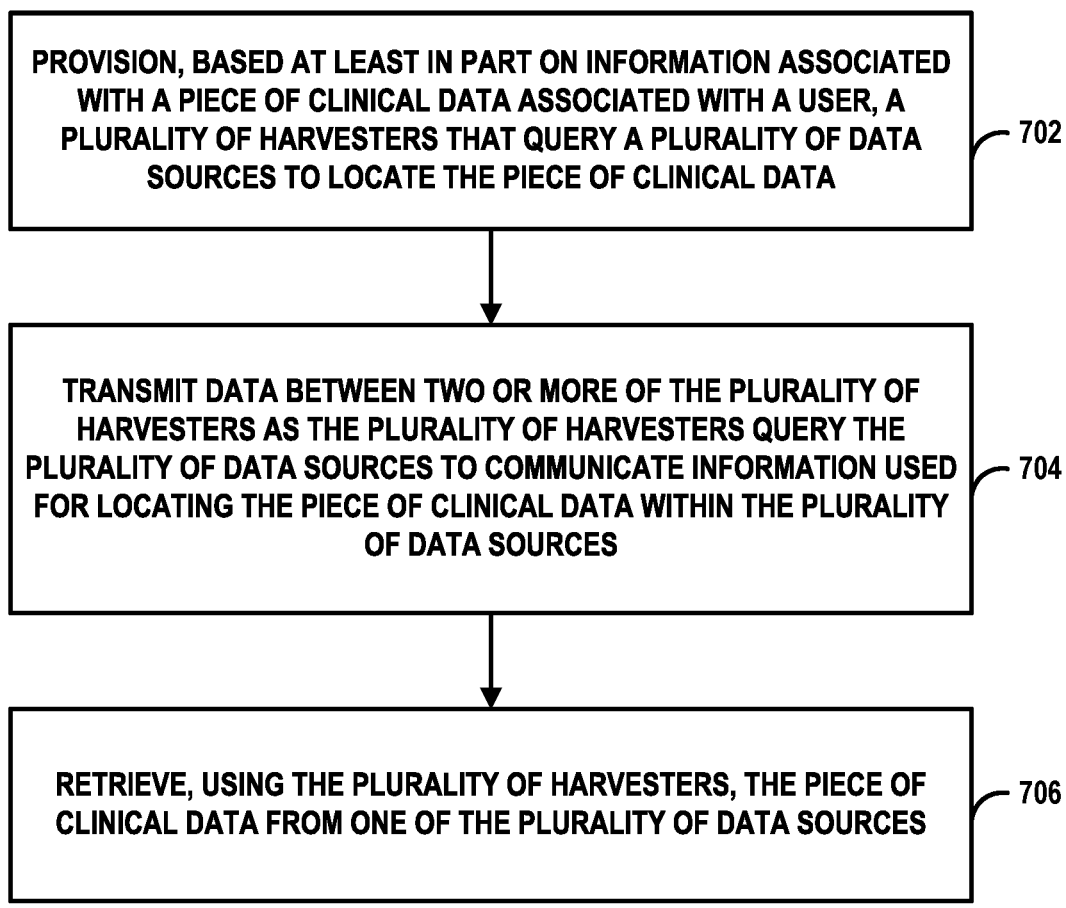
FIG. 7 is flow diagram illustrating example operations of an example clinical harvester system, in accordance with one or more aspects of the present disclosure.

FIG. 7 is flow diagram illustrating example operations of an example clinical harvester system, in accordance with one or more aspects of the present disclosure. For purposes of illustration only, the operations of FIG. 7 are described with reference to clinical harvester system 150 shown in FIGS. 1A and 1B.

As shown in FIG. 7, clinical harvester system 150 may provision, based at least in part on information associated with a piece of clinical data associated with a user, a plurality of harvesters 106 that query a plurality of data sources 114 to locate the piece of clinical data (702). For example, the plurality of harvesters 106 may be a plurality of serverless applications, and clinical harvester sys 150 may provision the plurality of harvesters 106 by executing the plurality of serverless applications in a plurality of virtual containers, such as Docker containers.

Clinical harvester system 150 may transmit data between two or more of the plurality of harvesters 106 as the plurality of harvesters 106 query the plurality of data sources 114 to communicate information used for locating the piece of clinical data within the plurality of data sources 114 (704). That is, as the plurality of harvesters 106 execute to query the plurality of data sources 114, the plurality of harvesters 106 may retrieve, from the plurality of data sources, data that may be relevant for finding the piece of clinical data. The plurality of harvesters 106 may therefore communicate with each other to exchange data that may be relevant for finding the piece of clinical data, and the plurality of harvesters 106 may use such data received from other harvesters to find the piece of clinical data.

Clinical harvester system 150 may retrieve, using the plurality of harvesters 106, the piece of clinical data from one of the plurality of data sources 114 (706).

In some examples, the piece of clinical data comprises immunization records for the user, and where to provision the plurality of harvesters 106, clinical harvester system 150 may provision a membership harvester that queries a first one or more data sources of the plurality of data sources 114 to retrieve information associated with the user, and may provision an immunization harvester that queries a second one or more data sources of the plurality of data sources 114 to retrieve the immunization records. In some examples, as part of transmitting data between two or more of the plurality of harvesters 106, clinical harvester system 150 may transmit the information associated with the user from the membership harvester to the immunization harvester, and the immunization harvester may use the information associated with the user to query the second one or more data sources for the immunization records.

In some examples, the plurality of data sources 114 comprise data sources internal to an organization associated with clinical harvester system 150, and wherein to provision the plurality of harvesters 106, clinical harvester system 150 may, in response to determining that the piece of clinical data cannot be located within the data sources internal to the organization, provision one or more harvesters that query one or more data sources external to the organization to locate the piece of clinical data.

In some examples, clinical harvester system 150 may determine confidence scores associated with information retrieved by the plurality of harvesters 106 from the plurality of data sources 114. The confidence scores may correspond with relevance of the information to finding the piece of clinical data. Clinical harvester system 150 may prioritize use of one or more of the information retrieved by the plurality of harvesters 106 for querying one or more of the plurality of data sources to find the piece of clinical data based at least in part on the confidence scores associated with the information retrieved by the plurality of harvesters 106.

In some examples, to determine the confidence scores associated with the information retrieved by the plurality of harvesters 106 from the plurality of data sources 114, clinical harvester system 150 may further determine a confidence score for a piece of information retrieved from a data source based at least in part on matching the piece of information with a keyword associated with the piece of clinical data.

In some examples, to provision the plurality of harvesters 106 that query the plurality of data sources 114, clinical harvester system 150 may determine, based at least in part on inputting information associated with the piece of clinical data into a learning engine 108 that includes one or more neural networks, one or more of the plurality of data sources 114 to query for the piece of clinical data, and clinical harvester system 150 may provision one or more of the plurality of harvesters 106 to query the one or more of the plurality of data sources 114 for the piece of clinical data.

In some examples, clinical harvester system 150 may train learning engine 108 using feedback from the plurality of harvesters 106 regarding whether one or more data sources contain the piece of clinical data.

In some examples, clinical harvester system 150 may track data lineage of the piece of clinical data and may determine, based on the data lineage of the piece of clinical data, a data delivery time for delivering the piece of clinical data. Clinical harvester system 150 may send the data delivery time to a system, such as portal 102, that is expecting delivery of the piece of clinical data from clinical harvester system 150, in order to inform the system expecting delivery of the piece of clinical data of the expected amount of time until the system may receive the data from clinical harvester system 150.

In some examples, clinical harvester system 150 may listen to a data stream for an indication that the piece of clinical data associated with the user is missing. That is, as the data stream is being outputted by, e.g., portal 102, clinical harvester system 150 may access, in real-time, the data stream to determine whether the data stream being outputted indicates that the piece of clinical data associated with the user is mission. Clinical harvester system 150 may, in in response to determining that the data stream includes the indication that the piece of clinical data associated with the user is missing, provision the plurality of harvesters 106 that query the plurality of data sources 114 to locate the piece of clinical data.

This disclosure includes the following examples.

Example 1: A method includes provisioning, by one or more processors of a clinical harvester system and based at least in part on information associated with a piece of clinical data associated with a user, a plurality of harvesters that query a plurality of data sources to locate the piece of clinical data; transmitting, by the one or more processors, data between two or more of the plurality of harvesters as the plurality of harvesters query the plurality of data sources to communicate information used for locating the piece of clinical data within the plurality of data sources; and retrieving, by the one or more processors and using the plurality of harvesters, the piece of clinical data from one of the plurality of data sources.

Example 2: The method of example 1, wherein: the piece of clinical data comprises immunization records for the user; provisioning the plurality of harvesters further comprises: provisioning, by the one or more processors, a membership harvester that queries a first one or more data sources of the plurality of data sources to retrieve information associated with the user, and provisioning, by the one or more processors, an immunization harvester that queries a second one or more data sources of the plurality of data sources to retrieve the immunization records; and transmitting the data between two or more of the plurality of harvesters further comprises: transmitting, by the one or more processors, the information associated with the user from the membership harvester to the immunization harvester, and using, by the immunization harvester executing at the one or more processors, the information associated with the user to query the second one or more data sources for the immunization records.

Example 3: The method of any of examples 1 and 2, wherein the plurality of data sources comprises data sources internal to an organization associated with the clinical harvester system, and wherein provisioning the plurality of harvesters further comprises: in response to determining that the piece of clinical data cannot be located within the data sources internal to the organization, provisioning, by one or more processors, one or more harvesters configured to query one or more data sources external to the organization to locate the piece of clinical data.

Example 4: The method of any of examples 1-3, further includes determining, by the one or more processors, confidence scores associated with information retrieved by the plurality of harvesters from the plurality of data sources, wherein the confidence scores correspond with relevance of the information to finding the piece of clinical data; and prioritizing, by the one or more processors, use of one or more of the information retrieved by the plurality of harvesters for querying one or more of the plurality of data sources to find the piece of clinical data based at least in part on the confidence scores associated with the information retrieved by the plurality of harvesters, including selecting, by the one or more processors, the one or more of the plurality of data sources to be queried based on the prioritization of the use of the one or more or the information.

Example 5: The method of example 4, wherein determining the confidence scores associated with the information retrieved by the plurality of harvesters from the plurality of data sources further comprises: determining, by the one or more processors, a confidence score for a piece of information retrieved from a data source based at least in part on matching the piece of information with a keyword associated with the piece of clinical data.

Example 6: The method of any of examples 1-5, wherein provisioning the plurality of harvesters that query the plurality of data sources further comprises: determining, by the one or more processors and based at least in part on inputting information associated with the piece of clinical data into a learning engine that includes one or more neural networks, one or more of the plurality of data sources to query for the piece of clinical data; and provisioning one or more of the plurality of harvesters to query the one or more of the plurality of data sources for the piece of clinical data.

Example 7: The method of example 6, further includes training, by the one or more processors, the learning engine using feedback from the plurality of harvesters regarding whether one or more data sources contain the piece of clinical data.

Example 8: The method of any of examples 1-7, further includes tracking, by the one or more processors, data lineage of the piece of clinical data; and determining, by the one or more processors and based on the data lineage of the piece of clinical data, a data delivery time for delivering the piece of clinical data.

Example 9: The method of any of examples 1-8, further includes listening, by the one or more processors, to a data stream for an indication that the piece of clinical data associated with the user is missing, wherein provisioning the plurality of harvesters comprises in response to determining that the data stream includes the indication that the piece of clinical data associated with the user is missing, provisioning, by the one or more processors the plurality of harvesters that query the plurality of data sources to locate the piece of clinical data.

Example 10: The method of any of examples 1-9, wherein the plurality of harvesters comprises a plurality of serverless applications, and wherein provisioning the plurality of harvesters comprises: executing, by the one or more processors, the plurality of serverless applications in a plurality of virtual containers.

Example 11: A clinical harvester system includes a memory; and one or more processors configured to: provision, based at least in part on information associated with a piece of clinical data associated with a user, a plurality of harvesters that query a plurality of data sources to locate the piece of clinical data; transmit data between two or more of the plurality of harvesters as the plurality of harvesters query the plurality of data sources to communicate information used for locating the piece of clinical data within the plurality of data sources; and retrieve, using the plurality of harvesters, the piece of clinical data from one of the plurality of data sources.

Example 12: The clinical harvester system of example 11, wherein the piece of clinical data comprises immunization records for the user; wherein to provision the plurality of harvesters, the one or more processors are further configured to: provision a membership harvester that queries a first one or more data sources of the plurality of data sources to retrieve information associated with the user, and provision an immunization harvester that queries a second one or more data sources of the plurality of data sources to retrieve the immunization records; and wherein to transmit the data between two or more of the plurality of harvesters, the one or more processors are further configured to: transmit the information associated with the user from the membership harvester to the immunization harvester, and use the information associated with the user to query the second one or more data sources for the immunization records.

Example 13: The clinical harvester system of any of examples 11 and 12, wherein the plurality of data sources comprises data sources internal to an organization associated with the clinical harvester system, and wherein to provision the plurality of harvesters, the one or more processors are further configured to: in response to determining that the piece of clinical data cannot be located within the data sources internal to the organization, provision one or more harvesters that query one or more data sources external to the organization to locate the piece of clinical data.

Example 14: The clinical harvester system of any of examples 11-13, wherein the one or more processors are further configured to: determine confidence scores associated with information retrieved by the plurality of harvesters from the plurality of data sources, wherein the confidence scores correspond with relevance of the information to finding the piece of clinical data; and prioritize use of one or more of the information retrieved by the plurality of harvesters for querying one or more of the plurality of data sources to find the piece of clinical data based at least in part on the confidence scores associated with the information retrieved by the plurality of harvesters, including selecting the one or more of the plurality of data sources to be queried based on the prioritization of the use of the one or more or the information.

Example 15: The clinical harvester system of example 14, wherein to determine the confidence scores associated with the information retrieved by the plurality of harvesters from the plurality of data sources, the one or more processors are further configured to: determine a confidence score for a piece of information retrieved from a data source based at least in part on matching the piece of information with a keyword associated with the piece of clinical data.

Example 16: The clinical harvester system of any of examples 11-15, wherein to provision the plurality of harvesters that query the plurality of data sources, the one or more processors are further configured to: determine, based at least in part on inputting information associated with the piece of clinical data into a learning engine that includes one or more neural networks, one or more of the plurality of data sources to query for the piece of clinical data; and provision one or more of the plurality of harvesters to query the one or more of the plurality of data sources for the piece of clinical data.

Example 17: The clinical harvester system of example 16, wherein the one or more processors are further configured to: train the learning engine using feedback from the plurality of harvesters regarding whether one or more data sources contain the piece of clinical data.

Example 18: The clinical harvester system of any of examples 11-17, wherein the one or more processors are further configured to: track data lineage of the piece of clinical data; and determine, based on the data lineage of the piece of clinical data, a data delivery time for delivering the piece of clinical data.

Example 19: The clinical harvester system of any of examples 11-18, wherein the one or more processors are further configured to listen to a data stream for an indication that the piece of clinical data associated with the user is missing, and wherein to provision the plurality of harvesters, the one or more processors are further configured to, in response to determining that the data stream includes the indication that the piece of clinical data associated with the user is missing, provision the plurality of harvesters that query the plurality of data sources to locate the piece of clinical data.

Example 20: A non-transitory computer-readable storage medium storing instructions that, when executed, cause one or more processors of a clinical harvester system to: provision, based at least in part on information associated with a piece of clinical data associated with a user, a plurality of harvesters that query a plurality of data sources to locate the piece of clinical data; transmit data between two or more of the plurality of harvesters as the plurality of harvesters query the plurality of data sources to communicate information used for locating the piece of clinical data within the plurality of data sources; and retrieve, using the plurality of harvesters, the piece of clinical data from one of the plurality of data sources.

By way of example, and not limitation, such computer-readable storage media can comprise RAM, ROM, EEPROM, CD-ROM or other optical disk storage, magnetic disk storage, or other magnetic storage devices, flash memory, or any other storage medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage mediums and media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable medium.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various embodiments have been described. These and other embodiments are within the scope of the following claims.

What is claimed is:
1. A computer-implemented method comprising:
   receiving, by one or more processors, a request to locate clinical data associated with a user;
   in response to receiving the request, starting, by the one or more processors, a first serverless application of a plurality of serverless applications in a cloud-based system that queries a first data source of a plurality of data sources to locate a piece of the clinical data;

in response to determining that the first serverless application is unable to locate the piece of the clinical data, starting, by the one or more processors, a second serverless application of the plurality of serverless applications in the cloud-based system that queries a second data source of the plurality of data sources to locate the piece of the clinical data;

transmitting, by the one or more processors, locative data between the first serverless application and the second serverless application, wherein the locative data is retrieved from the first data source, and wherein the locative data is used to locate the piece of the clinical data within the second data source; and receiving, by the one or more processors, the piece of the clinical data located by the second serverless application from the second data source.

2. The computer-implemented method of claim 1, wherein:

the piece of the clinical data comprises a health record of the user;

the first serverless application is a membership data harvester that queries a first one or more data sources of the plurality of data sources to retrieve second information associated with the user;

the second serverless application is an immunization data harvester that queries a second one or more data sources of the plurality of data sources to retrieve the health record;

transmitting the locative data between the first serverless application and the second serverless application further comprises sending, by the one or more processors, first information associated with the user from the membership data harvester to the immunization data harvester; and receiving the piece of the clinical data comprises querying, by the immunization data harvester using the first information associated with the user, the second one or more data sources for the health record.

3. The computer-implemented method of claim 1, wherein a first computing system comprises the first data source, and wherein the second data source is external to the first computing system.

4. The computer-implemented method of claim 1, further comprising:

determining, by the one or more processors, one or more confidence scores associated with third information, wherein the third information is retrieved by the plurality of serverless applications from the plurality of data sources, and the one or more confidence scores correspond to relevance of the third information to finding the piece of the clinical data;

prioritizing, by the one or more processors and based at least in part on the one or more confidence scores associated with the third information, use of one or more portions of the third information for querying one or more of the plurality of data sources to find the piece of the clinical data; and selecting, by the one or more processors and based on the prioritizing of the use of the one or more portions of the third information, the one or more of the plurality of data sources to be queried.

5. The computer-implemented method of claim 4, wherein determining the one or more confidence scores associated with the third information comprises:

determining, by the one or more processors, a confidence score, of the one or more confidence scores, for a piece of the third information retrieved from a data source based at least in part on matching the piece of the third information with a keyword associated with the piece of the clinical data.

6. The computer-implemented method of claim 1, wherein starting the second serverless application that queries the second data source comprises:

determining, by the one or more processors and based at least in part on inputting fourth information associated with the piece of the clinical data into a learning engine that includes one or more neural networks, one or more of the plurality of data sources to query for the piece of the clinical data; and using the second serverless application to query the one or more of the plurality of data sources for the piece of the clinical data.

7. The computer-implemented method of claim 6, further comprising:

training, by the one or more processors, the learning engine using feedback from the plurality of serverless applications regarding whether one or more of the plurality of data sources contain the piece of the clinical data.

8. The computer-implemented method of claim 1, further comprising:

determining, by the one or more processors and based on a data lineage of the piece of the clinical data, a data delivery time for delivering the piece of the clinical data.

9. The computer-implemented method of claim 1, further comprising:

monitoring, by the one or more processors, a data stream for an indication that the piece of the clinical data is missing, and wherein starting the first serverless application is performed, by the one or more processors, in response to determining that the data stream includes the indication that the piece of the clinical data is missing.

10. The computer-implemented method of claim 1, wherein starting the first serverless application and the second serverless application comprises:

executing, by the one or more processors, the first serverless application and the second serverless application in a plurality of virtual containers that performs ingestion, processing, and distribution of data.

11. A system comprising memory; and one or more processors communicatively coupled to the memory, the one or more processors configured to:

receive a request to locate clinical data associated with a user;

in response to receiving the request, start a first serverless application of a plurality of serverless applications in a cloud-based system that queries a first data source of a plurality of data sources to locate a piece of the clinical data;

in response to determining that the first serverless application is unable to locate the piece of the clinical data, start a second serverless application of the plurality of serverless applications in the cloud-based system that queries a second data source of the plurality of data sources to locate the piece of the clinical data;

transmit locative data between the first serverless application and the second serverless application, wherein the locative data is retrieved from the first data source, and wherein the locative data is used for locating the piece of the clinical data within the second data source; and receive the piece of the clinical data located by the second serverless application from the second data source.

12. The system of claim 11, wherein:
the piece of the clinical data comprises a health record of the user;
the first serverless application is a membership data harvester that queries a first one or more data sources of the plurality of data sources to retrieve second information associated with the user;
the second serverless application is an immunization data harvester that queries a second one or more data sources of the plurality of data sources to retrieve the health record;
to transmit the locative data between the first serverless application and the second serverless application, the one or more processors are further configured to send first information associated with the user from the membership data harvester to the immunization data harvester; and
to receive the piece of the clinical data, the one or more processors are further configured to query the second one or more data sources for the health record using the first information associated with the user.

13. The system of claim 11, wherein a first computing system comprises the first data source, and
wherein the second data source is external to the first computing system.

14. The system of claim 11, wherein the one or more processors are further configured to:
determine one or more confidence scores associated with third information, wherein the third information is retrieved by the plurality of serverless applications from the plurality of data sources, and the one or more confidence scores correspond to relevance of the third information to finding the piece of the clinical data;
prioritize, based at least in part on the one or more confidence scores associated with the third information, use of one or more portions of the third information for querying one or more of the plurality of data sources to find the piece of the clinical data; and
select, based on the prioritizing of the use of the one or more portions of the third information, the one or more of the plurality of data sources to be queried.

15. The system of claim 14, wherein to determine the one or more confidence scores associated with the third information, the one or more processors are further configured to:
determine a confidence score, of the one or more confidence scores, for a piece of the third information retrieved from a data source based at least in part on matching the piece of the third information with a keyword associated with the piece of the clinical data.

16. The system of claim 11, wherein to start the second serverless application that queries the second data source, the one or more processors are further configured to:
determine, based at least in part on inputting fourth information associated with the piece of the clinical data into a learning engine that includes one or more neural networks, one or more of the plurality of data sources to query for the piece of the clinical data; and
use the second serverless application to query the one or more of the plurality of data sources for the piece of the clinical data.

17. The system of claim 16, wherein the one or more processors are further configured to:
train the learning engine using feedback from the plurality of serverless applications regarding whether one or more of the plurality of data sources contain the piece of the clinical data.

18. The system of claim 11, wherein the one or more processors are further configured to:
determine, based on a data lineage of the piece of the clinical data, a data delivery time for delivering the piece of the clinical data.

19. The system of claim 11,
wherein the one or more processors are further configured to monitor a data stream for an indication that the piece of the clinical data is missing, and wherein the one or more processors are configured to start the first serverless application in response to determining that the data stream includes the indication that the piece of the clinical data is missing.

20. One or more non-transitory computer-readable storage media including instructions that, when executed by one or more processors, cause the one or more processors to:
receive a request to locate clinical data associated with a user;
in response to receiving the request, start a first serverless application of a plurality of serverless applications in a cloud-based system that queries a first data source of a plurality of data sources to locate a piece of the clinical data;
in response to determining that the first serverless application is unable to locate the piece of the clinical data, start a second serverless application of the plurality of serverless applications in the cloud-based system that queries a second data source of the plurality of data sources to locate the piece of the clinical data;
transmit locative data between the first serverless application and the second serverless application, wherein the locative data is retrieved from the first data source, and wherein the locative data is used for locating the piece of the clinical data within the second data source; and
receive the piece of the clinical data located by the second serverless application from the second data source.

* * * * *